(12) United States Patent
Edmunds et al.

(10) Patent No.: US 10,385,048 B2
(45) Date of Patent: Aug. 20, 2019

(54) PESTICIDALLY ACTIVE POLYCYCLIC DERIVATIVES WITH SULFUR CONTAINING SUBSTITUENTS

(71) Applicant: Syngenta Participations AG, Basel (CH)

(72) Inventors: Andrew Edmunds, Stein (CH); Pierre Joseph Marcel Jung, Stein (CH); Michel Muehlebach, Stein (CH); Long Lu, Shanghai (CN); Yaming Wu, Shanghai (CN); Ruifang Chen, Shanghai (CN)

(73) Assignee: SYNGENTA PARTICIPATION AG, Basel (CH)

( * ) Notice: Subject to any disclaimer, the term of this patent is extended or adjusted under 35 U.S.C. 154(b) by 0 days.

(21) Appl. No.: 15/540,378

(22) PCT Filed: Dec. 28, 2015

(86) PCT No.: PCT/EP2015/081255
§ 371 (c)(1),
(2) Date: Jun. 28, 2017

(87) PCT Pub. No.: WO2016/107831
PCT Pub. Date: Jul. 7, 2016

(65) Prior Publication Data
US 2017/0367332 A1  Dec. 28, 2017

(30) Foreign Application Priority Data
Dec. 31, 2014 (WO) ................ PCT/CN2014/095773

(51) Int. Cl.
*A01N 43/90* (2006.01)
*C07D 471/04* (2006.01)
(52) U.S. Cl.
CPC ........... *C07D 471/04* (2013.01); *A01N 43/90* (2013.01)
(58) Field of Classification Search
CPC .. C07D 471/04; C07D 498/04; C07D 513/04; A01N 43/90
See application file for complete search history.

(56) References Cited

U.S. PATENT DOCUMENTS 4,603,139 A * 7/1986 King .................... C07D 471/04
514/337

FOREIGN PATENT DOCUMENTS

| WO | 2008009348 A1 | 1/2008 |
| WO | 2013018928 A1 | 2/2013 |
| WO | 2013180194 A1 | 12/2013 |
| WO | 2014104407 A1 | 7/2014 |
| WO | 2014119672 A1 | 8/2014 |
| WO | 2014178363 A1 | 11/2014 |
| WO | 2015121136 A1 | 8/2015 |

OTHER PUBLICATIONS

International Search Report and Written Opinion for PCT/EP2015/081255, dated Feb. 15, 2016.

* cited by examiner

*Primary Examiner* — John Pak
(74) *Attorney, Agent, or Firm* — Baker & Hostetler LLP; Toni-Junell Herbert

(57) ABSTRACT

Compounds of formula (I), wherein the substituents are as defined in claim 1, and the agrochemically acceptable salts salts, stereoisomers, enantiomers, tautomers and N-oxides of those compounds, can be used as insecticides and can be prepared in a manner known per se.

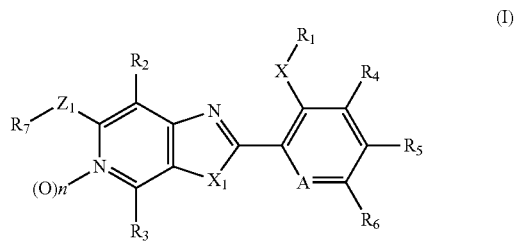

(I)

10 Claims, No Drawings

PESTICIDALLY ACTIVE POLYCYCLIC DERIVATIVES WITH SULFUR CONTAINING SUBSTITUENTS

RELATED APPLICATION INFORMATION

This application is a 371 of International Application No. PCT/EP2015/081255, filed 28 Dec. 2015, which claims priority to PCT/CN2014/095773, filed 31 Dec. 2014, the contents of which are incorporated herein by reference herein.

The present invention relates to pesticidally active, in particular insecticidally active polycyclic derivatives containing sulfur substituents, to intermediates for the preparation of those compounds, to compositions comprising those compounds, and to their use for controlling animal pests (including arthropods and in particular insects or representatives of the order Acarina).

Heterocyclic compounds with pesticidal action are known and described, for example, in WO 2012/086848, and WO 2013/018928. There have now been found novel pesticidally active tricyclic ring derivatives with sulfur containing phenyl and pyridyl substituents.

The present invention accordingly relates to compounds of formula I,

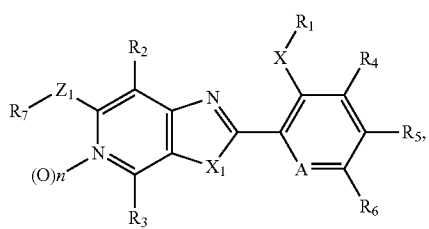

(I)

wherein
A is CH, N, or NO;
X is S, SO or $SO_2$;
$X_1$ is O, S, or $N(C_1-C_3alkyl)$;
$R_1$ is $C_1-C_6alkyl$, $C_1-C_6haloalkyl$, $C_3-C_6cycloalkyl$, $C_3-C_6cycloalkyl-C_1-C_6alkyl$; or
$R_1$ is $C_3-C_6cycloalkyl-C_1-C_6alkyl$ mono- or polysubstituted by substituents selected from the group consisting of halogen, cyano and $C_1-C_4alkyl$; or
$R_1$ is $C_2-C_6alkenyl$, $C_2-C_6haloalkenyl$ or $C_2-C_6alkynyl$;
$R_2$ is hydrogen, or $C_1-C_3alkyl$;
$R_3$ is hydrogen, or $C_1-C_3$-alkyl;
$R_4$ and $R_6$ is hydrogen or $C_1-C_3alkyl$;
$R_5$ is hydrogen, Halogen, $C_1-C_6alkyl$, $C_1-C_6haloalkyl$, $C_1-C_6haloalkoxy$, $C_1-C_6alkylsulfanyl$, $C_1-C_6alkylsulfinyl$, $C_1-C_6alkylsulfonyl$, $C_1-C_6haloalkylsulfanyl$, $C_1-C_6haloalkylsulfinyl$, $C_1-C_6haloalkylsulfonyl$, or $C_3-C_6cycloalkyl-C_1-C_4alkyl$;
$Z_1$ is oxygen, S, SO or $SO_2$, with the proviso that when $R_7$ is hydrogen, $Z_1$ is different from SO and $SO_2$;
$R_7$ is hydrogen, $C_1-C_6alkyl$, $C_1-C_6haloalkyl$, $C_2-C_6alkenyl$, $C_2-C_6haloalkenyl$ or $C_2-C_6alkynyl$, $C_2-C_6haloalkynyl$, $C_1-C_6alkylcyano$, $C_3-C_6cycloalkyl$, $C_3-C_6halocycloalkyl$, $C_3-C_6cycloalkyl-C_1-C_4alkyl$, or $C_3-C_6cycloalkyl-C_1-C_4alkyl$ mono- or polysubstituted by substituents selected from the group consisting of halogen, cyano and $C_1-C_4alkyl$;
n is 0 or 1;
and agrochemically acceptable salts, stereoisomers, enantiomers, tautomer's and N-oxides of those compounds.

Compounds of formula I which have at least one basic centre can form, for example, acid addition salts, for example with strong inorganic acids such as mineral acids, for example perchloric acid, sulfuric acid, nitric acid, a phosphorus acid or a hydrohalic acid, with strong organic carboxylic acids, such as $C_1-C_4alkanecarboxylic$ acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1-C_4alkane-$ or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, and their branched isomers.

Alkylsulfanyl, alkylsulfinyl, alkylsulfonyl, alkoxy, alkenyl and alkynyl radicals are derived from the alkyl radicals mentioned.

The alkenyl and alkynyl groups can be mono- or polyunsaturated. $C_2-C_6alkenyl$ and $C_2-C_6haloalkenyl$ groups are those which have a chain length of 2 to 5 carbon atoms, and $C_2-C_6haloalkenyl$ groups, where halogen is fluorine, chlorine, bromine and iodine, and in particular fluorine and chlorine, are for example 1-chlorovinyl, 2-chlorovinyl, 2,2-difluorovinyl, 2,2-difluoroprop-1-en-2-yl, 2,2-dichlorovinyl, 3-fluoroprop-1-enyl, chloroprop-1-en-1-yl, 3-bromoprop-1-en-1-yl, 2,3,3-trifluoroprop-2-en-1-yl, 2,3,3-trichloroprop-2-en-1-yl and 4,4,4-trifluorobut-2-en-1-yl. Suitable as haloalkynyl are, for example, monohalogenated or polyhalogenated alkynyl groups, where halogen is bromine, iodine and, in particular, fluorine and chlorine, for example 3-fluoropropynyl, 3-chloropropynyl, 3-bromopropynyl, 3,3,3-trifluoropropynyl and 4,4,4-trifluorobut-2-yn-1-yl.

Alkoxy groups preferably have a chain length of 1 to 6 carbon atoms. Alkoxy is, for example, methoxy, ethoxy, propoxy, i-propoxy, n-butoxy, iso-butoxy, sec-butoxy and tert-butoxy and the pentyloxy and hexyloxy isomers; preferably methoxy and ethoxy.

Halogen is generally fluorine, chlorine, bromine or iodine. This also applies, correspondingly, to halogen in combination with other meanings, such as haloalkyl.

Haloalkyl groups with a chain length of 1 up to 6 carbon atoms are, for example, fluoromethyl, difluoromethyl, trifluoromethyl, chloromethyl, dichloromethyl, trichloromethyl, 2,2,2-trifluoroethyl, 1-fluoroethyl, 2-fluoroethyl, 2-chloroethyl, 2-fluoroprop-2-yl, pentafluoroethyl, 1,1-difluoro-2,2,2-trichloroethyl, 2,2,3,3-tetrafluoroethyl and 2,2,2-trichloroethyl, pentafluoroethyl, heptafluoro-n-propyl, perfluoro-n-hexyl; haloalkyl groups in the meanings $R_7$, and $R_5$ are preferably bromo(difluoro)methyl, trichloromethyl, fluoromethyl, dichlorofluoromethyl, difluorochloromethyl, difluoromethyl, trifluoromethyl, pentafluoroethyl or heptafluoro-n-propyl.

Haloalkoxy groups preferably have a chain length of from 1 to 6 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy, bromo(difluoro)methoxy, and trifluoromethoxy.

Alkylsulfany groups preferably have a chain length of 1 to 8 carbon atoms. Alkylthio is, for example, methylthio, ethylthio, propylthio, iso-propylthio, n-butylthio, iso-butylthio, sec-butylthio or tert-butylthio, preferably methylthio and ethylthio. The alklysulfanyl can be mono or polysubstituted by halogen atoms.

Alkylsulfinyl is, for example, methylsulfinyl, ethylsulfinyl, propylsulfinyl, iso-propylsulfinyl, n-butylsulfinyl, iso-butylsulfinyl, sec-butylsulfinyl, tert-butylsulfinyl; preferably methylsulfinyl and ethylsulfinyl. The alklysulfinyl can be mono or polysubstituted by halogen atoms.

Alkylsulfonyl is, for example, methylsulfonyl, ethylsulfonyl, propylsulfonyl, iso-propylsulfonyl, n-butylsulfonyl, iso-butylsulfonyl, sec-butylsulfonyl or tert-butylsulfonyl; preferably methylsulfonyl or ethylsulfonyl. The alklysulfonyl can be mono or polysubstituted by halogen atoms.

The cycloalkyl groups preferably have from 3 to 6 ring carbon atoms, for example cyclopropyl, cyclobutyl, cyclopentyl and cyclohexyl.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

The compounds of formula I according to the invention also include hydrates which may be formed during the salt formation.

A preferred group of compounds of formula I is represented by the compounds of formula I-1

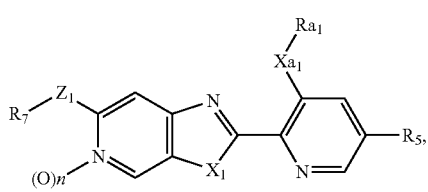
(I-1)

wherein $R_5$, $R_7$, $Z_1$, n and $X_1$ are as defined under formula I above; and wherein $Xa_1$ is S, SO or $SO_2$; $Ra_1$ is methyl, ethyl, n-propyl, i-propyl or cyclopropylmethyl; and agrochemically acceptable salts, stereoisomers, enantiomers, tautomers of those compounds.

In this preferred group of compounds of formula I-1, $R_5$ is preferably is hydrogen, Halogen, $C_1$-$C_3$haloalkyl, $C_1$-$C_3$haloalkoxy, $C_1$-$C_3$alkylsulfanyl, $C_1$-$C_3$alkylsulfinyl, $C_1$-$C_3$alkylsulfonyl, $C_1$-$C_3$haloalkylsulfanyl, $C_1$-$C_3$haloalkylsulfinyl, $C_1$-$C_3$haloalkylsulfonyl, $Xa_1$ is preferably $SO_2$, $Ra_1$ is preferably ethyl, $X_1$ is preferably N-methyl, $Z_1$ is oxygen or sulfur, n is 0 or 1, and $R_7$ is $C_1$-$C_3$haloalkyl, $C_2$-$C_4$haloalkenyl, $C_2$-$C_4$haloalkynyl, $C_3$-$C_6$halocycloalkyl, or $C_3$-$C_6$cycloalkyl-$C_1$-$C_4$alkyl mono- or polysubstituted by halogen.

More highly preferred compounds of formula I-1 are those in which $R_5$ is hydrogen or $C_1$-$C_3$haloalkyl, $Xa_1$ is $SO_2$, $Ra_1$ is ethyl, $X_1$ is preferably N-methyl, $Z_1$ is oxygen, S, SO, $SO_2$, n is 0, and $R_7$ is $C_1$-$C_3$haloalkyl.

A further preferred group of compounds of formula I is represented by compounds of formula I-2:

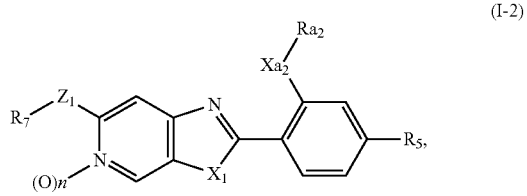
(I-2)

wherein $R_5$, $R_7$, $Z_1$, n and $X_1$ are as defined under formula I above; and wherein $Xa_1$ is S, SO or $SO_2$; $Ra_1$ is methyl, ethyl, n-propyl, i-propyl or cyclopropylmethyl; and agrochemically acceptable salts, stereoisomers, enantiomers, tautomers of those compounds.

In this preferred group of compounds of formula I-1, $R_5$ is preferably is hydrogen, Halogen, $C_1$-$C_3$haloalkyl, $C_1$-$C_3$haloalkoxy, $C_1$-$C_3$alkylsulfanyl, $C_1$-$C_3$alkylsulfinyl, $C_1$-$C_3$alkylsulfonyl, $C_1$-$C_3$haloalkylsulfanyl, $C_1$-$C_3$haloalkylsulfinyl, $C_1$-$C_3$haloalkylsulfonyl, $Xa_1$ is preferably $SO_2$, $Ra_1$ is preferably ethyl, $X_1$ is preferably N-methyl, $Z_1$ is oxygen or sulfur, n is 0 or 1, and $R_7$ is $C_1$-$C_3$haloalkyl, $C_2$-$C_4$haloalkenyl, $C_2$-$C_4$haloalkynyl, $C_3$-$C_6$halocycloalkyl, or $C_3$-$C_6$cycloalkyl-$C_1$-$C_4$alkyl mono- or polysubstituted by halogen.

More highly preferred compounds of formula I-2 are those in which $R_5$ is hydrogen or $C_1$-$C_3$haloalkyl, $Xa_1$ is $SO_2$, $Ra_1$ is ethyl, $X_1$ is preferably N-methyl, $Z_1$ is oxygen, S, SO or $SO_2$, n is 0, and $R_7$ is $C_1$-$C_3$haloalkyl.

In a preferred group of compounds of formula I,
A is N;
X is S or $SO_2$;
$X_1$ is N($C_1$-$C_3$alkyl);
$R_1$ is $C_1$-$C_6$alkyl, preferably ethyl;
$R_2$, $R_3$, $R_4$ and $R_6$ are hydrogen;
$Z_1$ is oxygen, S, SO or $SO_2$; in particular S or SO;
$R_5$ is $C_1$-$C_4$haloalkyl or halogen; and
$R_7$ is $C_1$-$C_4$alkyl, which can be substituted by cyano, or $R_7$ is $C_1$-$C_4$haloalkyl; preferably $R_7$ is $C_1$-$C_4$haloalkyl; and preferably n is 0.

The process according to the invention for preparing compounds of formula I is carried out by methods known to those skilled in the art. For example, compounds of formula Ia;

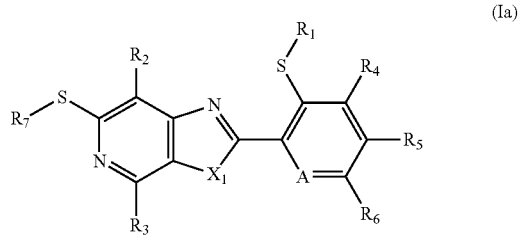
(Ia)

wherein $R_7$, $R_6$, $R_5$, $R_4$, $R_3$, $R_2$, $R_1$, $X_1$, and A are as defined in formula I, can be prepared from compounds of formula II

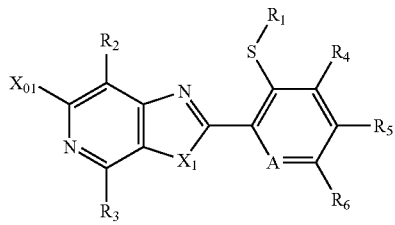

(II)

wherein A, $R_1$, $R_2$, $R_3$, $R_4$, $R_5$, $R_6$, X, and $X_1$, are as described in formula I, and $X_{01}$ is halogen, by reaction with (bpy)CuSR$_7$, wherein $R_7$ is $C_1$-$C_3$ haloalkyl (prepared as described in the experimental section) in an inert solvent (such as acetonitrile) at temperatures between 25° C.-120° C. Such chemistry is known and has been described in the literature (*Angew. Chem. Int. Ed.* 2013, 52, 1548-1552). Compounds of formula Ia, can be further oxidized to compounds of formula Ib, Ic, Id, Ie, If, Ig, and Ih by methods known to those skilled in the art and analogous to those described in WO 2013/018928 and WO 2012/086848 and shown in Scheme 1.

Scheme 1.

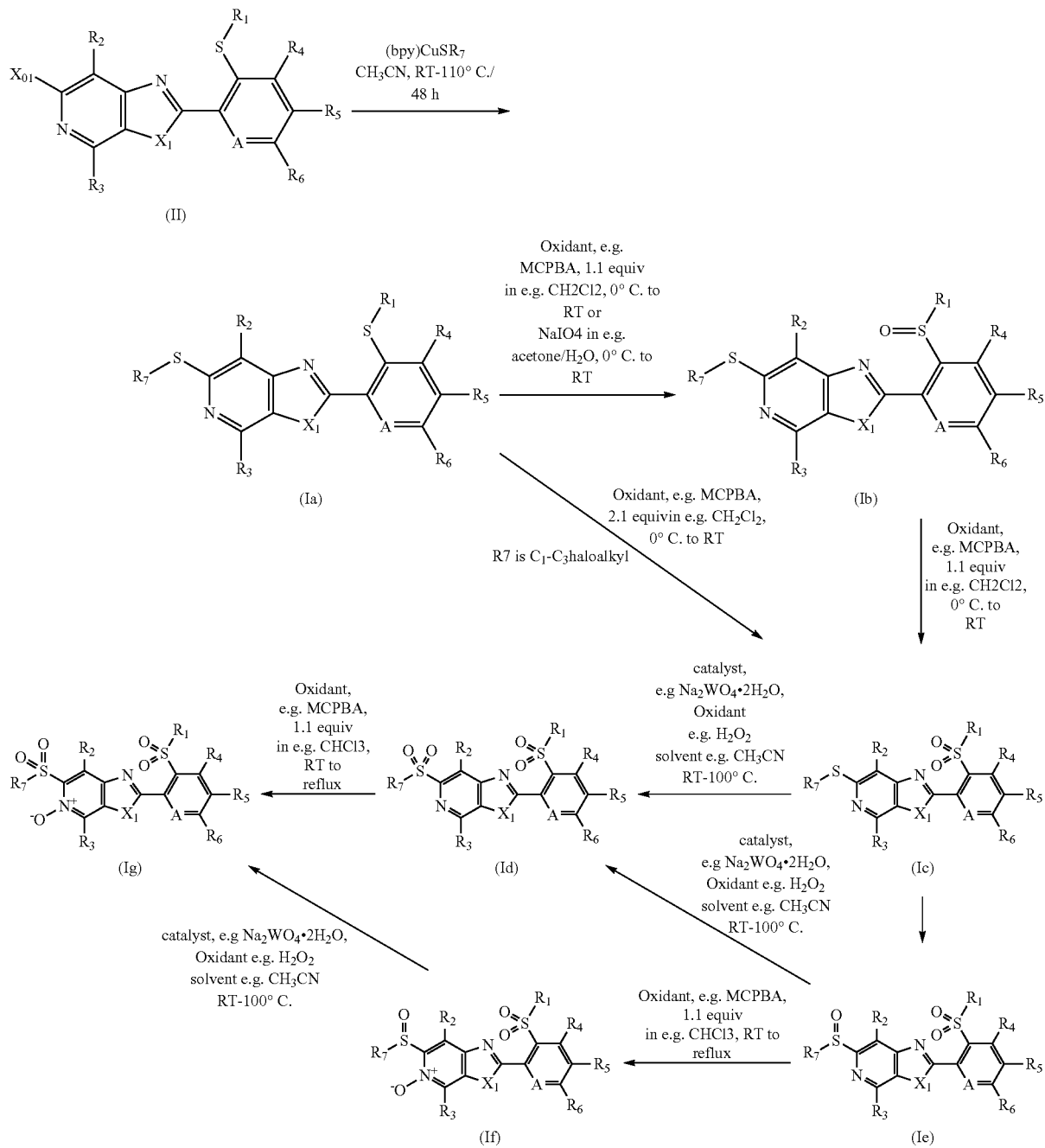

Thus, the compound of formula Ia can be oxidized to a compound of formula Ib, by treating for example with sodium periodate or m-chloroperbenzoic acid, in an inert solvent such as dichloromethane and chloroform, alcohols such as methanol and ethanol, acetic acid, water, and mixtures thereof. The amount of the oxidant to be used in the reaction is generally 1 to 3 moles, preferably 1 to 1.1 moles, relative to 1 mole of the present compound Ia. The reaction temperature of the reaction is generally within a range of 0° C. to room temperature. The compound represented by the formula (Ic) can be produced by reacting the compound (Ia) in the presence of an oxidant, such as m-chloroperbenzoic acid, in an inert solvent. Examples of the solvent to be used in the reaction include aliphatic halogenated hydrocarbons such as dichloromethane and chloroform; alcohols such as methanol and ethanol; acetic acid; water; and mixtures thereof. Examples of the oxidant to be used in the reaction include m-chloroperbenzoic acid hydrogen peroxide solution. The amount of the oxidant to be used in the reaction is generally 1 to 4 moles, preferably 2.1 moles, relative to 1 mole of the present compound (Ia). The reaction temperature of the reaction is generally within a range of 0° C. to rt. The reaction may be conducted in the presence of a catalyst. Examples of the catalyst to be used in the reaction include sodium tungstate. The $SR_7$ group wherein $R_7$ is C1-C3-haloalkyl is more difficult to oxidize and so compounds of Id, If, Ig, Ih, and Ie generally require higher temperature with oxidants such as m-chloroperbenzoic acid or a hydrogen peroxide solution in the presence of a catalyst, for example sodium tungstate. Those skilled in the art will appreciate that the degree and position of oxidation will depend on such factors as equivalents of oxidant and reaction temperature. Those skilled in the art will also appreciate that even if mixtures of products are formed, these can be separated by crystallization or chromatographic techniques, and the position and degree of oxidation can be determined by spectroscopic methods such as mass spectroscopy, NMR techniques and $^{13}C$-$^1H$ coupling constants. In a similar manner, compounds of formula Ic, Id, Ie, Ig, and If can be obtained starting from compounds of formula IIa;

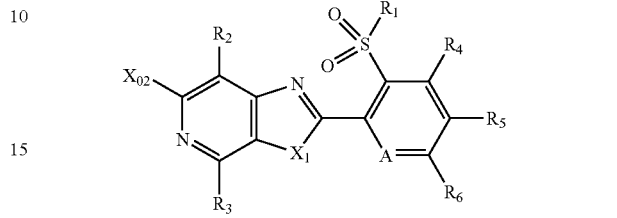

wherein A, $R_1$, $R_2$, $R_3$, $R_4$, $R_5$, $R_6$, X, and $X_1$, are as described in formula I, and $X_{02}$ is halogen, by reaction with (bpy)$CuSR_7$ to give a compound of formula Ic, and subsequent oxidation by the methods described in scheme 1.

A further synthesis of compounds of formula I is illustrated in scheme 3:

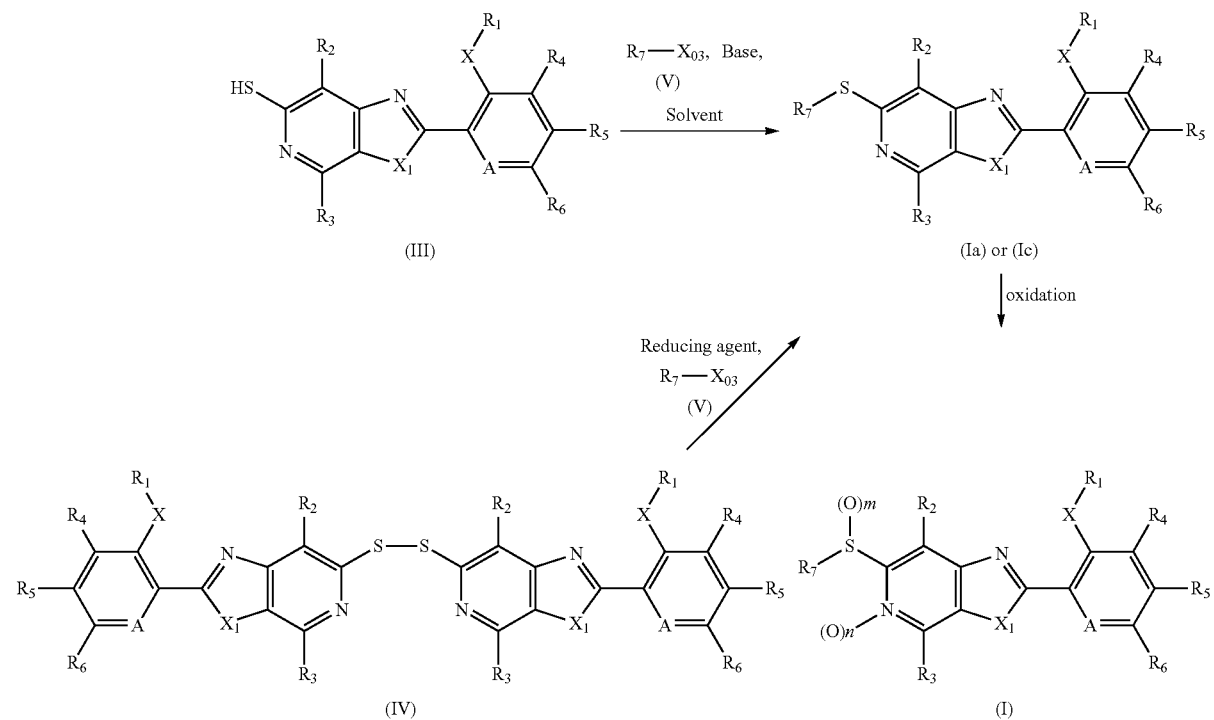

Thus, a compound of formula III, wherein A, $R_1$, $R_2$, $R_3$, $R_4$, $R_5$, $R_6$, X, and $X_1$, are as described in formula I, with a compound of formula V wherein $R_7$ is as described in formula I (but not hydrogen), and $X_{03}$ is a leaving group, such as chlorine atom, a bromine atom, an iodine atom, a trifluoromethanesulfonyloxy group and a methanesulfonyloxy group. The reaction is generally conducted in the presence of a base in a solvent, such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; and mixtures thereof. Examples of the base to be used in the reaction include alkali metal or alkaline earth metal hydrides such as sodium hydride, potassium hydride, calcium hydride; inorganic bases such as sodium carbonate and potassium carbonate; and organic bases such as triethylamine. The intermediate compound may also be a disulfide, of formula IV. In this case, the reaction with compound V is generally conducted in the presence of a reductant. Examples of the reductant to be used in the reaction include sodium hydroxymethanesulfinate (trade name: Rongalite), or sodium borohydride. Analogous reactions have been well described in the literature (see for example WO 2013018928). Compounds of formula Ia and Ic can be further oxidized to compounds of formula I wherein A, $R_1$, $R_2$, $R_3$, $R_4$, $R_5$, $R_6$, X, n, and $X_1$ are as described in formula I, and m is 0, 1, or 2 as described in scheme 1. Compounds of formula I wherein $R_7$ is a $C_1$-$C_6$ perfluoroalkyl group can be produced by reacting the intermediate compound (IV), perfluoroalkyl iodide and a reductant. The reaction is generally conducted in the presence of a solvent. Examples of the solvent to be used in the reaction include ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; and mixtures thereof. Examples of the reductant to be used in the reaction include tetrakis (dimethylamino) ethylene. Examples of the perfluoroalkyl iodide to be used in the reaction include trifluoromethane iodide, pentafluoroethane iodide, heptafluoro-2-iodopropane, and the like. The reaction temperature of the reaction is generally within a range of −80° C. to 50° C. The compounds so formed can then further be transformed to compounds of formula I wherein $Z_1$ is SO or $SO_2$ and n is 0, 1, or 2 by oxidation as described in scheme 1.

The compound of formula III can be produced by reacting a compound of formula IIb, wherein A, $R_1$, $R_2$, $R_3$, $R_4$, $R_5$, $R_6$, X, and $X_1$, are as described in formula I, and $X_{04}$ is a halogen, with a sulfating agent. The intermediate compound (IV), which is a disulfide of the compound (III), can be produced oxidizing the compound of formula (III). This is shown in scheme 4.

The compound of formula III can be produced by reacting the compound (IIb) with a thioesterificating agent and a catalyst. The reaction is generally conducted in the presence of a solvent. Examples of the solvent to be used in the reaction include aromatic hydrocarbons such as toluene and xylene; aprotic polar solvents such as DMF, NMP, and DMSO; and mixtures thereof. Examples of the thioesterificating agent to be used in the reaction include sodium sulfide, sodium sulfide 9-hydrate, and thiourea. Examples of the catalyst to be used in the reaction include copper (I) chloride, copper (I) bromide, and copper (I) iodide. The reaction may be conducted in the presence of a ligand. Examples of the ligand to be used in the reaction include acetylacetone, salen, phenanthroline, and the like. The reaction may be conducted in the presence of a base. Examples of the base to be used in the reaction include inorganic bases such as potassium carbonate, cesium carbonate, and tripotassium phosphate; and organic bases, for example triethylamine. The intermediate compound (IV) can be produced by reacting the present compound (III) with an oxidant. The reaction is generally conducted in the presence of a solvent. Examples of the solvent to be used in the reaction include water; alcohols such as methanol and ethanol; ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; carboxylic acids such as acetic acid; and mixtures thereof. Examples of the oxidant to be used in the reaction include oxygen, iodine, hydrogen peroxide solution, potassium ferricyanide, and the like.

The compound of formula III can also be produced by thioesterifying the present compound of formula IIb to give the intermediate compound of formula (VI), and then hydrolyzing the resulting intermediate compound (VI), as shown in scheme 5.

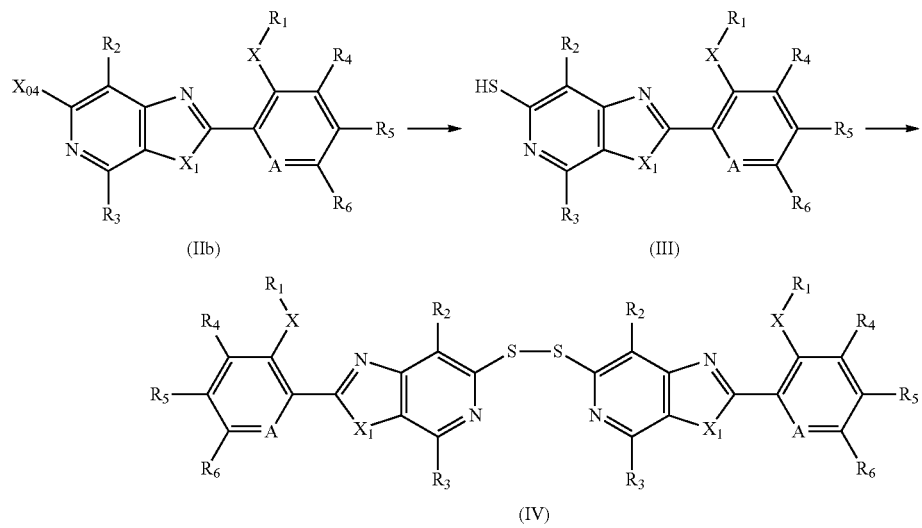

Scheme 4.

Scheme 5.

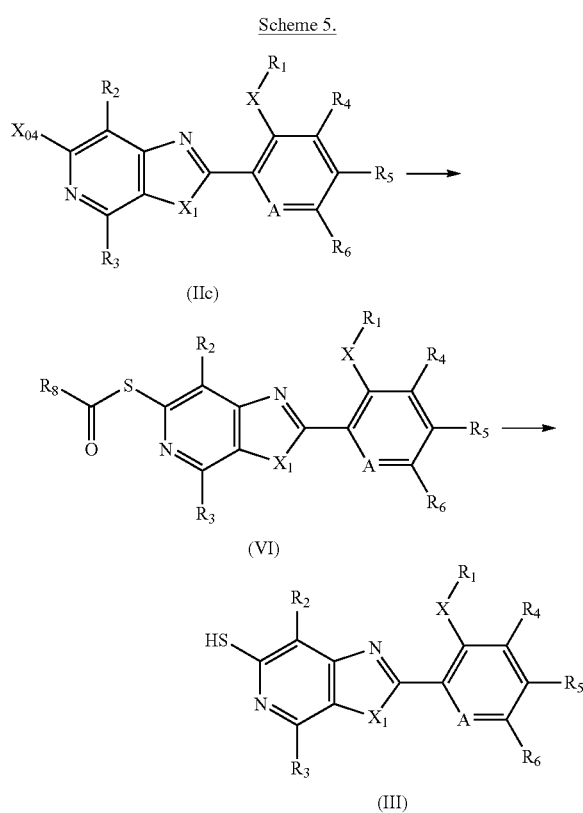

In scheme 5, $R_8$ is any of the groups other than a hydrogen atom for $R_7$ in the formula (I), and additionally phenyl. The other symbols are as defined in the formula (I). The intermediate compound (VI) can be produced by reacting the compound (IIb) with a thioesterifying agent, in the presence of a base and a catalyst. The reaction is generally conducted in the presence of a solvent. Examples of the solvent to be used in the reaction include aromatic hydrocarbons such as toluene and xylene; aprotic polar solvents such as DMF, NMP, and DMSO; and mixtures thereof. Examples of the thioesterifying agent to be used in the reaction include thiobenzoic acid, and the like. Examples of the catalyst to be used in the reaction include copper (I) chloride, copper (I) bromide, and copper (I) iodide. The reaction may be conducted in the presence of a ligand. Examples of the ligand to be used in the reaction include acetylacetone, salen, phenanthroline; and the like. Examples of the base to be used in the reaction include inorganic bases such as potassium carbonate, cesium carbonate, and tripotassium phosphate; and organic bases such as triethylamine. The reaction temperature of the reaction is generally within a range of 50° C. to 200° C. In the reaction, $X_{04}$ is preferably a bromine atom and an iodine atom. The present compound (III) can be produced by hydrolyzing the intermediate compound (VI). When the hydrolysis is conducted in the presence of an acid, an aqueous solution of the acid is generally used as a solvent. Examples of the acid to be used in the reaction include mineral acids such as hydrochloric acid, nitric acid, phosphoric acid, and sulfuric acid; and carboxylic acids such as acetic acid and trifluoroacetic acid. When the hydrolysis of compound (VI) is conducted in the presence of a base, the reaction is generally conducted in the presence of a solvent. Examples of the solvent to be used in the reaction include ethers such as THF, ethylene glycol dimethyl ether, tert-butylmethyl ether, and 1,4-dioxane; alcohols such as methanol and ethanol; water; and mixtures thereof. Examples of the base to be used in the reaction include alkali metal hydroxides such as sodium hydroxide and potassium hydroxide.

Compounds of formula I wherein $Z_1$ is oxygen, i.e. compounds of formula Ii, can be prepared as shown in scheme 6:

Scheme 6.

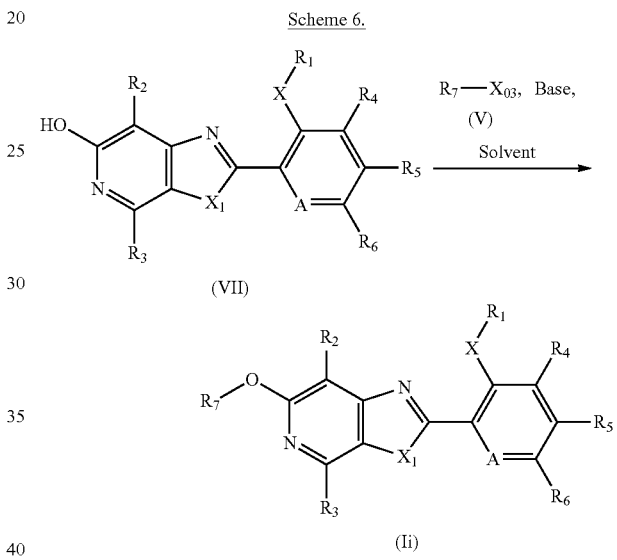

Thus, a compound of formula VII, wherein A, $R_1$, $R_2$, $R_3$, $R_4$, $R_5$, $R_6$, X, and $X_1$, are as described in formula I, with a compound of formula V wherein $R_7$ is as described in formula I (but not hydrogen), and $X_{03}$ is a leaving group, such as chlorine atom, a bromine atom, an iodine atom, a trifluoromethanesulfonyloxy group and a methanesulfonyloxy group. The reaction is generally conducted in the presence of a base in a solvent, such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; and mixtures thereof. Examples of the base to be used in the reaction include alkali metal or alkaline earth metal hydrides such as sodium hydride, potassium hydride, calcium hydride; inorganic bases such as sodium carbonate and potassium carbonate; and organic bases such as triethylamine. Compounds of formula Ii wherein X is sulfur can be further oxidized to compounds of formula I wherein A, $R_1$, $R_2$, $R_3$, $R_4$, $R_5$, $R_6$, X, n, and $X_1$ are as described in formula I, and X is SO or $SO_2$ and n is 0 or 1 as described in scheme 1.

The compound of formula (Ij) wherein $R_7$ is a trifluoromethyl group can be prepared by the process shown in scheme 7.

Scheme 7

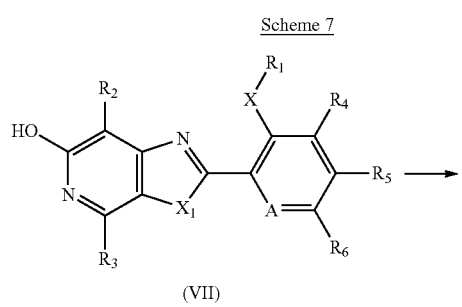

(VII)

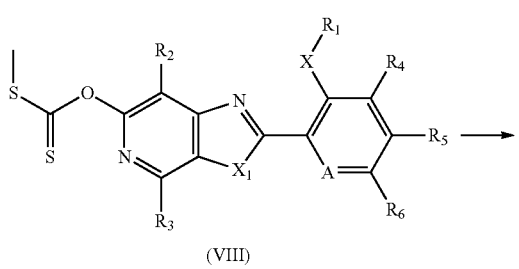

(VIII)

the presence of a solvent. Examples of the solvent to be used in the reaction include aprotic polar-solvents such as DMF, NMP, and DMSO. Examples of the base to be used in the reaction include alkali metal hydrides such as sodium hydride. Examples of the methylating agent to be used in the reaction include methyl iodide. The reaction temperature of the reaction is generally within a range of 0° C. to 100° C.

The present compound (Ij) wherein $R_7$ is a trifluoromethyl group can be produced by reacting the intermediate compound (VIII) with a fluorinating agent in the presence of a base. The reaction is conducted in the presence of a solvent. Examples of the solvent to be used in the reaction include halogenated hydrocarbons such as dichloromethane, chloroform, carbon tetrachloride, and 1,2-dichloro ethane. The reaction is conducted in the presence of a base and a fluorinating agent. Examples of the base to be used in the reaction include 1,3-dibromo-5, 5-dimethyl hydantoin. Examples of the fluorinating agent to be used in the reaction include tetra-n-butylammonium fluoride, and hydrogen fluoride pyridine complex. The reaction temperature of the reaction is generally within a range of −80° C. to 50° C.

The compound of formula VII can be produced via the intermediate compound (IIb) as shown in scheme 8.

Scheme 8.

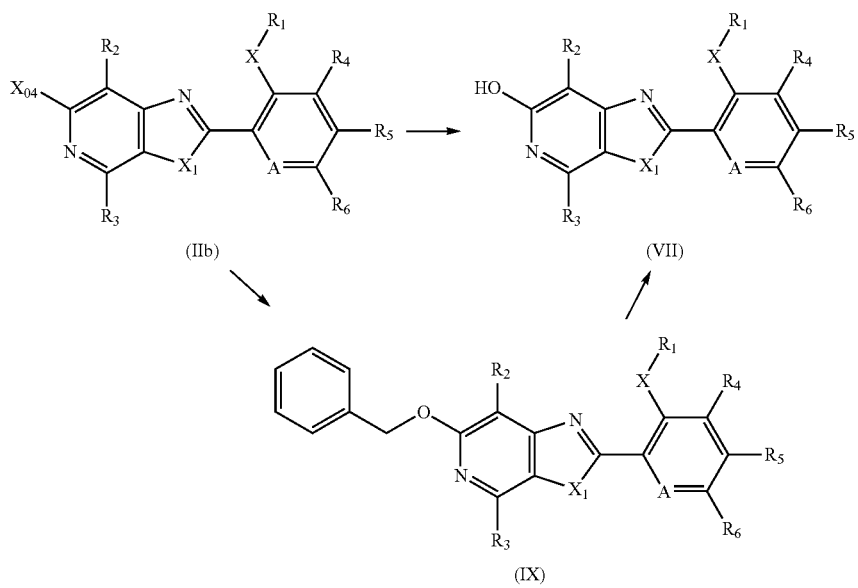

-continued

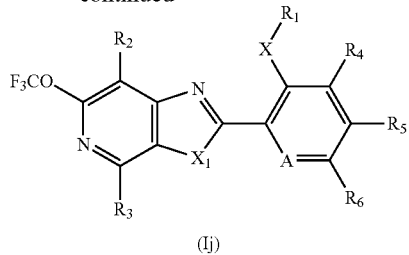

(Ij)

The intermediate compound (VIII) can be produced by reacting the present compound (VII), a base, carbon disulfide and a methylating agent. The reaction is conducted in Thus, a compound of formula IIb, wherein $X_{04}$ represents a halogen atom, and the other symbols are as defined in the formula (I) by reacting the compound (IIb) with benzyl alcohol in the presence of a base to give the intermediate compound of formula IX. The reaction is generally conducted in the presence of a solvent or used benzyl alcohol as a solvent. Examples of the solvent to be used in the reaction include aromatic hydrocarbons such as toluene and xylene; aprotic polar solvents such as DMF, NMP, and DMSO; and mixtures thereof. The reaction may be conducted in the presence of a catalyst. Examples of the catalyst to be used in the reaction include copper (I) chloride, copper (I) bromide, and copper (I) iodide. The reaction may be conducted in the presence of a ligand. Examples of the ligand to be used in the reaction include acetylacetone, salen, phenanthroline;

and the like. The reaction is generally conducted in the presence of a base. Examples of the base to be used in the reaction include inorganic bases such as potassium carbonate, cesium carbonate, and tripotassium phosphate. The compound of formula (VII) can be produced by reacting the intermediate compound (IX) with hydrogen in the presence of a hydrogenating catalyst. The reaction is generally conducted in the presence of a solvent under of hydrogen atmosphere at 1 to 100 atm. Examples of the solvent to be used in the reaction include ethers such as THF, ethylene glycol dimethyl ether, tert-butylmethyl ether, and 1,4-dioxane; esters such as ethyl acetate and butyl acetate; alcohols such as methanol and ethanol; water; and mixtures thereof. Examples of the hydrogenating catalyst to be used in the reaction include transition metal compounds such as palladium carbon, palladium hydroxide, Raney nickel, and platinum oxide. Alternatively, compounds of formula VII can be produced directly from IIb by treatment with a base, for example tripotassium phosphate and a catalyst, such as Copper(I)iodide and a ligand such as N,N'-dimethyl-1,2-ethylenediamine in water at temperatures between 50-100° C. Similar reactions have been described in WO 2013018928 and *Catalysis Communications*, 12(1), 64-66; 2010.

Compounds of formula IIc can be prepared (scheme 9) by reacting compounds of formula X and compounds of formula XI under various formal dehydration conditions, wherein A, $R_1$, $R_2$, $R_3$, $R_4$, $R_5$, $R_6$, X, $X_1$ and A have the values defined in formula I, and $X_{04}$ is halogen. These methods are known to those skilled in the art or described for example in WO 2009/131237, WO 2011/043404, WO 2011/040629, WO 2010/125985, WO 2012/086848, WO 2013/018928, WO 2013/191113, WO 2013/180193 and WO 2013/180194. Such processes are well known and have been described for example in WO 2011/040629 or WO 2009/131237 ($X_1$ is oxygen), WO 2011088990 or *Inorg. Chimica Acta*, 358(9), 2701-2710; 2005 ($X_1$ is sulfur) and *J. Am. Chem. Soc.*, 132(5), 1545-1557, 2010 or WO 2008/128968 ($X_1$ is $N(C_1\text{-}C_3Alkyl)$).

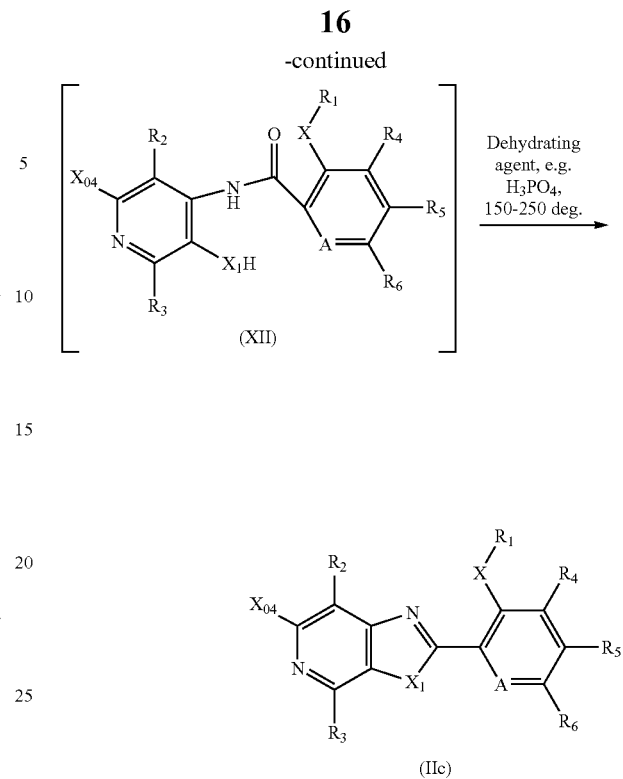

The process describing the reaction between compounds of formula X and compounds of formula XI towards compounds of formula IIc is summarized in more details in scheme 10:

Scheme 10

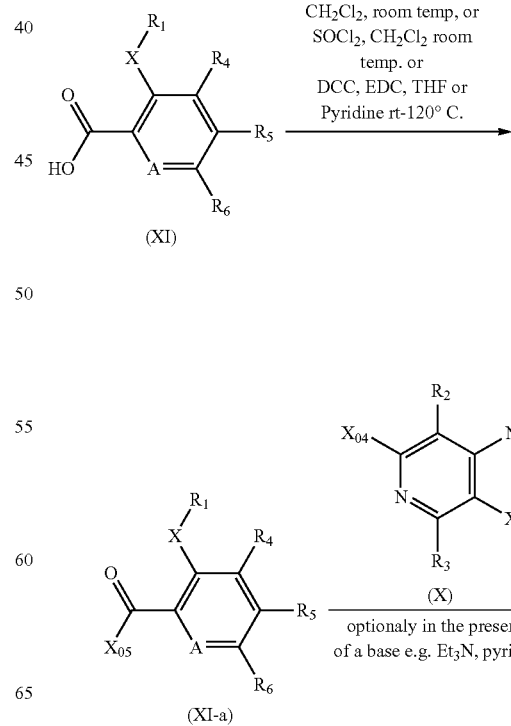

Scheme 9

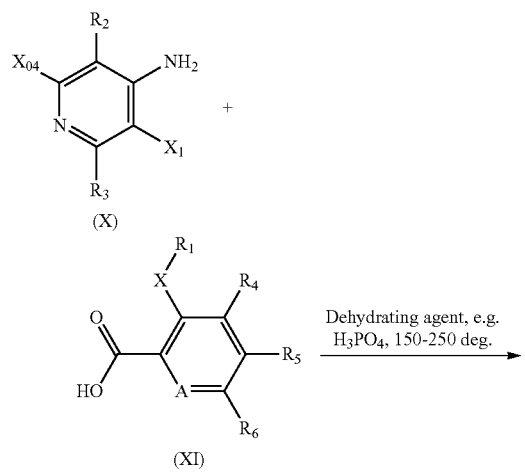

-continued

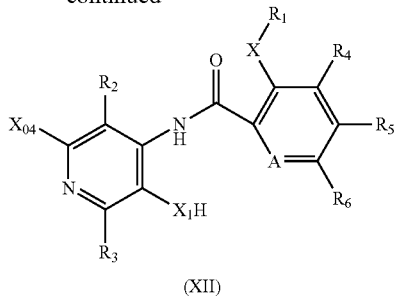

(XII)

PPh₃, DIAD, solvent, e.g. THF
r.t to 50° C. or
p-TsOH, inert solvent, e.g
NMP, Microwave, rt to 180° C.

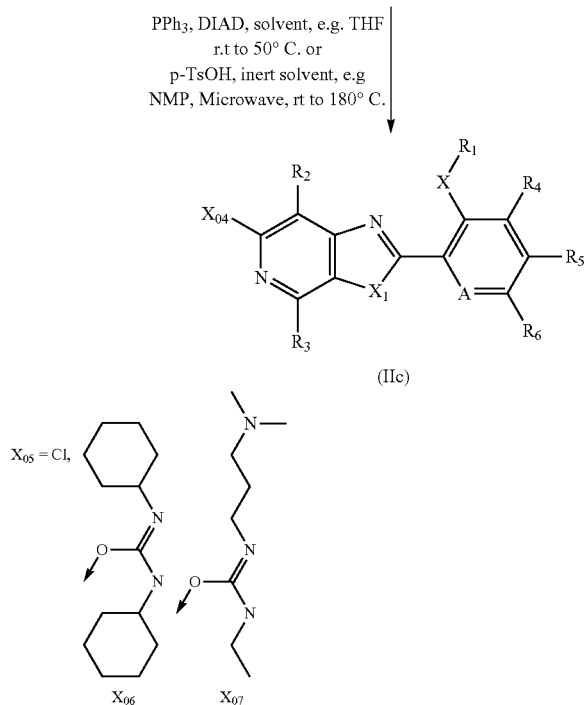

(IIc)

$X_{05}$ = Cl,

Compounds of formula XI, wherein A, $R_1$, $R_4$, $R_5$, $R_6$, X, and A have the values defined in formula I, are activated (scheme 10) to compounds of formula XI-a by methods known to those skilled in the art and described in for example *Tetrahedron*, 61 (46), 10827-10852, 2005. For example compounds where $X_{05}$ is chlorine are formed by treatment with for example, oxalyl chloride or thionyl chloride in the presence of catalytic quantities of DMF in inert solvents such as methylene chloride or THF at temperatures between 20° C. to 100° C., preferably 25° C. Treatment of XI-a with compounds of formula X, wherein $R_2$, $R_3$ and $X_1$ are as described in formula I, and X04 is halogen, optionally in the presence of a base, e.g. triethylamine or pyridine, leads to compounds of formula XII. Alternatively, compounds of formula IIc can be prepared by treatment of compounds of formula XI with dicyclohexyl carbodiimide (DCC) or 1-ethyl-3-(3-dimethylaminopropyl)carbodiimide (EDC) to give the activated species XI-a, wherein $X_{05}$ is $X_{06}$ and $X_{07}$ respectively, in an inert solvent, e.g. pyridine, or tetrahydrofuran (THF) optionally in the presence of a base, e.g. triethylamine, at temperatures between 50-180° C. Compounds of formula XII so obtained can then be converted to compounds of formula IIc by dehydration, eg. by heating the compounds under microwave irradiation, in the presence of an acid catalyst, for example methanesulfonic acid, or para-toluenesulfonic acid, in an inert solvent such as N-methyl pyrrolidone at temperatures between 25-180° C., preferably 130-170° C. Such processes have been described previously in WO 2010/125985. Alternatively, compounds of formula XII can be converted to compounds of formula IIc (wherein $X_1$ is O) using triphenylphosphine, di-isopropyl azodicarboxylate in an inert solvent such as THF at temperatures between 25-50° C. Such Mitsunobu conditions have been previously described for such transformations (see WO 2009/131237).

Compounds of formula (XI), wherein A, $R_1$, $R_4$, $R_5$, $R_6$, and X, have the values described in formula I and A is nitrogen are either known or can be prepared by methods described in WO 2014132971, WO 2014123205, WO 2014119670, WO 2014119679, WO 2014119674, WO 2014119494, WO 2014119699, WO 2014119672, WO 2014104407, WO 2014021468, WO 2013018928 and US 20100234603.

Compounds of formula (XI), wherein A, $R_1$, $R_4$, $R_5$, $R_6$, and X, have the values described in formula I and A is methine are either known or can be prepared by methods described in JP 2014024840, JP 2014024839, WO 2014002754, WO 2013191041, WO 2013191189, WO 2013187424, WO 2013187426, WO 2013187422, WO 2013187423, WO 2013187425, and WO 2012086848.

Compounds of formula (X) can be prepared by the methods shown, for example, in scheme 11.

Scheme 11.

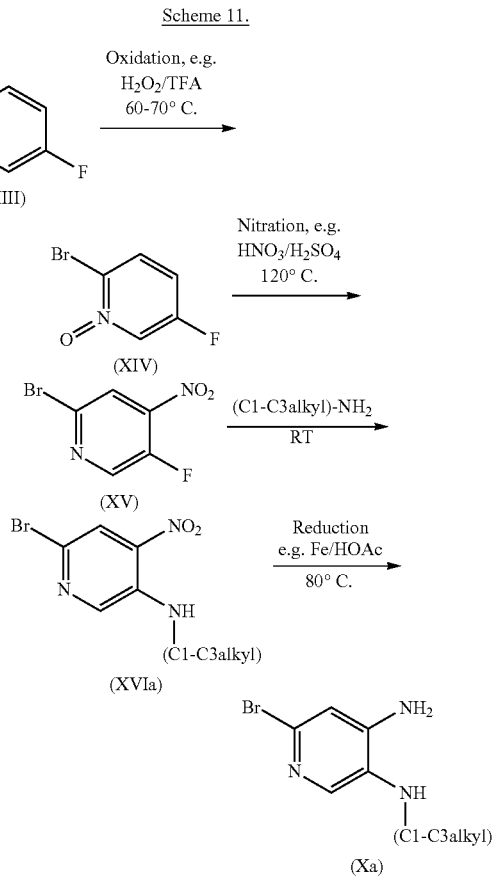

In scheme 11, a compound of formula (XIII) is oxidized to a compound of formula XIV by methods known to those skilled in the art, for example with hydrogen peroxide in trifluoroacetic acid and the like. The compounds of formula XIV can be nitrated by methods described for example in "Nitro Compounds, Aromatic" Ullmann's Encyclopedia of Industrial Chemistry, 2005, Wiley-VCH, Weinheim. Compounds of formula XV can be converted to compounds of formula XVIa by treatment with $(C_1-C_3Alkyl)NH_2$. The reaction is generally conducted in the presence of a solvent, such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; and mixtures thereof. The reaction temperature of the reaction is generally within a range of –80° C. to 50° C. The products of formula XVIa, can be reduced to compounds of formula Xa by methods known to those skilled in the art, for example with a metal in acidic medium, for example Fe in acetic acid or hydrochloric acid. Such reductions of $NO_2$ groups have been described for example in Org. Synth.; Coll. Vol. 5: 346, 1973.

Compounds of formula X wherein $X_1$ is O (i.e. compounds of formula Xb) can be produced from compounds of formula XV by treatment with a base, for example alkaline earth metal bases in water, NMP, DMF, 2-Imidazolidinone, or mixtures thereof at temperatures between 50-100° C. Reduction of the produced XVIb as described in scheme 11 leads to compounds of formula Xb. Similar reactions have been described in WO 2010/044411. The chemistry is summarized in scheme 12.

VIII wherein X1 is OH can be prepared from compounds of formula XV by treatment with aqueous base such as sodium hydroxide, or lithium hydroxide under conditions known to those skilled in the art. The nitro group of the compounds XVIb obtained can then be reduced to yield compounds of formula Xb using for example Fe in acetic acid or hydrochloric acid, as described in scheme 11.

For preparing all other compounds of the formula (I) functionalized according to the definitions of formula I, there are a large number of suitable known standard methods, for example alkylation, halogenation, acylation, amidation, oximation, oxidation and reduction, the choice of the preparation methods which are suitable depending on the properties (reactivity) of the substituents in the intermediates. The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium Scheme 12:

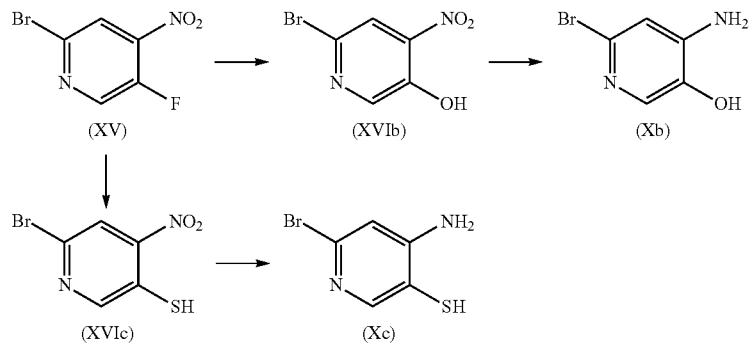

The compound of formula X wherein $X_1$ is SH (i.e. compounds of formula Xc) can be produced by reacting a compound of formula XV with a sulfating agent. Examples of the sulfating agent to be used in the reaction include sodium sulfide, sodium sulfide 9-hydrate, and thiourea. The reaction may be conducted in the presence of a base. Examples of the base to be used in the reaction include inorganic bases such as potassium carbonate, cesium carbonate, and tripotassium phosphate; and organic bases, for example triethylamine. The reaction is generally conducted in the presence of a solvent. Examples of the solvent to be used in the reaction include water; alcohols such as methanol and ethanol; ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; carboxylic acids such as acetic acid; and mixtures thereof. Similar reactions have been described in the literature (see WO 2010/055004). Reduction of the nitro group in compound XVIc as described in scheme 11 leads to compounds of formula Xc. The chemistry is summarized in scheme 12. In a similar manner, compounds of formula acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU). The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately –80° C. to approximately +140° C., preferably from approximately –30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture. Depending on the procedure or the reaction conditions, the compounds of formula I, which have salt-forming properties, can be obtained in free form or in the form of salts.

The compounds of formula I and, where appropriate, the tautomer's thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.* 1989, 32, 2561 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 20 below can be prepared according to the methods described above. The examples which follow are intended to illustrate the invention and show preferred compounds of formula I. "Ph" represents the phenyl group.

Table X: This table discloses the 32 substituent designations X.001 to X.032 for the formulae (Iaa), (Iab), (Iac), (Iad), (Iae) and (Iaf) which are disclosed after Table X. In table X, Et represents $CH_2CH_3$, $CH_2Cyp$ represents

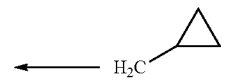

where the arrow represents the point of attachment to the sulfur.

TABLE X

| Comp. No | $R_1$ | $R_5$ | $R_7$ |
| --- | --- | --- | --- |
| X.001 | $CH_2CH_3$ | $CF_3$ | $CF_3$ |
| X.002 | $CH_2CH_3$ | $CF_3$ | $CF_2CF_3$ |
| X.003 | $CH_2CH_3$ | $CF_2CF_3$ | $CF_3$ |
| X.004 | $CH_2CH_3$ | $CF_2CF_3$ | $CF_2CF_3$ |
| X.005 | $CH_2CH_3$ | $OCHF_2$ | $CF_3$ |
| X.006 | $CH_2CH_3$ | $OCHF_2$ | $CF_2CF_3$ |
| X.007 | $CH_2CH_3$ | H | $CF_3$ |
| X.008 | $CH_2CH_3$ | H | $CF_2CF_3$ |
| X.009 | $CH_2CH_3$ | $CF_3$ | $CH_3$ |
| X.010 | $CH_2CH_3$ | $CF_3$ | $CH_2CH_3$ |
| X.011 | $CH_2CH_3$ | $CF_2CF_3$ | $CH_3$ |
| X.012 | $CH_2CH_3$ | $CF_2CF_3$ | $CH_2CH_3$ |
| X.013 | $CH_2CH_3$ | $OCHF_2$ | $CH_3$ |
| X.014 | $CH_2CH_3$ | $OCHF_2$ | $CH_2CH_3$ |
| X.015 | $CH_2CH_3$ | H | $CH_3$ |

TABLE X-continued

| Comp. No | $R_1$ | $R_5$ | $R_7$ |
|---|---|---|---|
| X.016 | $CH_2CH_3$ | H | $CH_2CH_3$ |
| X.017 | $CH_2CH_3$ | $CF_3$ | $CH=CH_2$ |
| X.018 | $CH_2CH_3$ | $CF_2CF_3$ | $CH=CH_2$ |
| X.019 | $CH_2CH_3$ | $OCHF_2$ | $CH=CH_2$ |
| X.020 | $CH_2CH_3$ | H | $CH=CH_2$ |
| X.021 | $CH_2CH_3$ | $CF_3$ | $CH_2CHF_2$ |
| X.022 | $CH_2CH_3$ | $CF_2CF_3$ | $CH_2CHF_2$ |
| X.023 | $CH_2CH_3$ | $OCHF_2$ | $CH_2CHF_2$ |
| X.024 | $CH_2CH_3$ | H | $CH_2CHF_2$ |
| X.025 | $CH_2CH_3$ | $CF_3$ | $CH_2CF_3$ |
| X.026 | $CH_2CH_3$ | $CF_2CF_3$ | $CH_2CF_3$ |
| X.027 | $CH_2CH_3$ | $OCHF_2$ | $CH_2CF_3$ |
| X.028 | $CH_2CH_3$ | H | $CH_2CF_3$ |
| X.029 | $CH_2CH_3$ | $CF_3$ | $CH_2CN$ |
| X.030 | $CH_2CH_3$ | $CF_2CF_3$ | $CH_2CN$ |
| X.031 | $CH_2CH_3$ | $OCHF_2$ | $CH_2CN$ |
| X.032 | $CH_2CH_3$ | H | $CH_2CN$ |

Table 1:

This table discloses the 32 compounds 1.001 to 1.032 of the formula (Iaa):

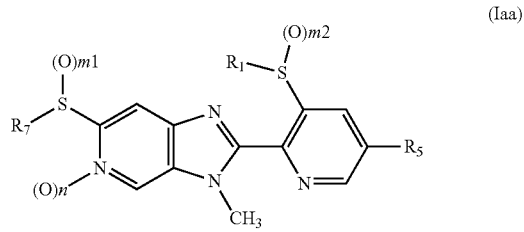

(Iaa)

wherein n is 0, m1 is 0, m2 is 0, and $R_1$, $R_5$, and $R_7$ are as defined in lines X.001-X.032 in table X. For example, compound 1.004 has the following structure:

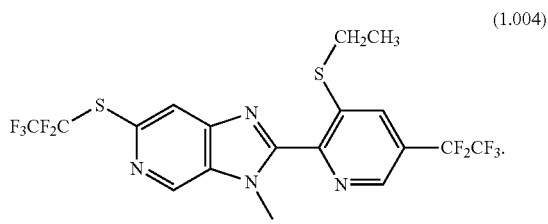

(1.004)

Table 2:

This table discloses the 32 compounds 2.001 to 2.032 of the formula (Iaa), wherein n is 0, m1 is 0, m2 is 2, and $R_1$, $R_5$, and $R_7$ are as defined in lines X.001-X.032 in table X.

Table 3:

This table discloses the 32 compounds 3.001 to 3.032 of the formula (Iaa), wherein n is 1, m1 is 0, m2 is 2, and $R_1$, $R_5$, and $R_7$ are as defined in lines X.001-X.032 in table X.

Table 4:

This table discloses the 32 compounds 4.001 to 4.032 of the formula (Iaa), wherein n is 1, m1 is 1, m2 is 2, and $R_1$, $R_5$, and $R_7$ are as defined in lines X.001-X.032 in table X.

Table 5:

This table discloses the 32 compounds 5.001 to 5.032 of the formula (Iaa), wherein n is 0, m1 is 2, m2 is 2, and $R_1$, $R_5$, and $R_7$ are as defined in lines X.001-X.032 in table X.

Table 6:

This table discloses the 32 compounds 6.001 to 6.032 of the formula (Iaa), wherein n is 1, m1 is 1, m2 is 2, and $R_1$, $R_5$, and $R_7$ are as defined in lines X.001-X.032 in table X.

Table 7:

This table discloses the 32 compounds 7.001 to 7.032 of the formula (Iab), wherein n is 0, m1 is 0, m2 is 0, and $R_1$, $R_5$, and $R_7$ are as defined in lines X.001-X.032 in table X.

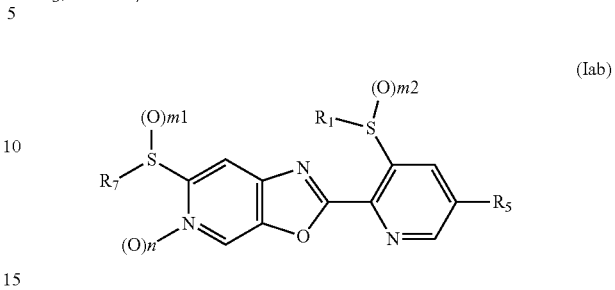

(Iab)

Table 8:

This table discloses the 32 compounds 8.001 to 8.032 of the formula (Iab), wherein n is 0, m1 is 0, m2 is 2, and $R_1$, $R_5$, and $R_7$ are as defined in lines X.001-X.032 in table X.

Table 9:

This table discloses the 32 compounds 9.001 to 9.032 of the formula (Iab), wherein n is 0, m1 is 2, m2 is 2, and $R_1$, $R_5$, and $R_7$ are as defined in lines X.001-X.032 in table X.

Table 10:

This table discloses the 32 compounds 10.001 to 10.032 of the formula (Iac), wherein n is 0, m1 is 0, m2 is 0, and $R_1$, $R_5$, and $R_7$ are as defined in lines X.001-X.032 in table X.

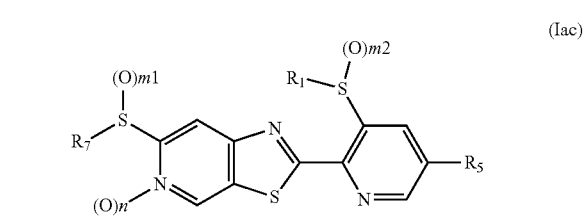

(Iac)

Table 11:

This table discloses the 32 compounds 11.001 to 11.032 of the formula (Iac), wherein n is 0, m1 is 0, m2 is 2, and $R_1$, $R_5$, and $R_7$ are as defined in lines X.001-X.032 in table X.

Table 12:

This table discloses the 32 compounds 12.001 to 12.032 of the formula (Iad):

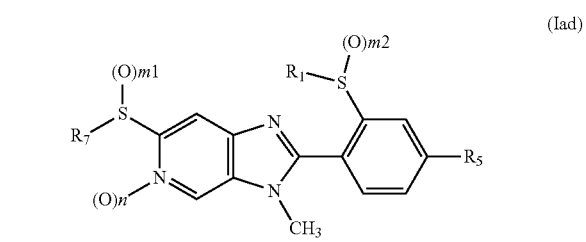

(Iad)

wherein n is 0, m1 is 0, m2 is 0, and $R_1$, $R_5$, and $R_7$ are as defined in lines X.001-X.032 in table X.

Table 13:

This table discloses the 32 compounds 13.001 to 13.032 of the formula (Iad), wherein n is 0, m1 is 0, m2 is 2, and $R_1$, $R_5$, and $R_7$ are as defined in lines X.001-X.032 in table X.

Table 14:

This table discloses the 32 compounds 14.001 to 14.032 of the formula (Iad), wherein n is 1, m1 is 0, m2 is 2, and $R_1$, $R_5$, and $R_7$ are as defined in lines X.001-X.032 in table X.

Table 15:

This table discloses the 32 compounds 15.001 to 15.032 of the formula (Iad), wherein n is 1, m1 is 1, m2 is 2, and $R_1$, $R_5$, and $R_7$ are as defined in lines X.001-X.032 in table X.

Table 16:

This table discloses the 32 compounds 16.001 to 16.032 of the formula (Iad), wherein n is 0, m1 is 2, m2 is 2, and $R_1$, $R_5$, and $R_7$ are as defined in lines X.001-X.032 in table X.

Table 17:

This table discloses the 32 compounds 17.001 to 17.032 of the formula (Iae), wherein n is 0, m1 is 0, m2 is 0, and $R_1$, $R_5$, and $R_7$ are as defined in lines X.001-X.032 in table X.

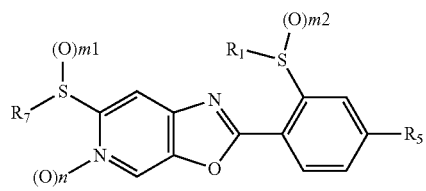

(Iae)

Table 18:

This table discloses the 32 compounds 18.001 to 18.032 of the formula (Iae), wherein n is 0, m1 is 0, m2 is 2, and $R_1$, $R_5$, and $R_7$ are as defined in lines X.001-X.032 in table X.

Table 19:

This table discloses the 32 compounds 19.001 to 19.032 of the formula (Iae), wherein n is 0, m1 is 2, m2 is 2, and $R_1$, $R_5$, and $R_7$ are as defined in lines X.001-X.032 in table X.

Table 20:

This table discloses the 32 compounds 20.001 to 20.032 of the formula (Iaf), wherein n is 0, m1 is 0, m2 is 0, and $R_1$, $R_5$, and $R_7$ are as defined in lines X.001-X.032 in table X.

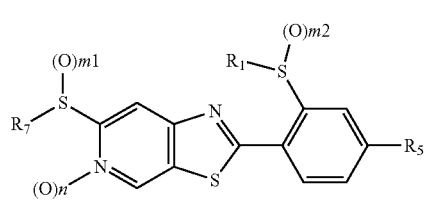

(Iaf)

Table 21:

This table discloses the 32 compounds 21.001 to 21.032 of the formula (Iaf), wherein n is 0, m1 is 0, m2 is 2, and $R_1$, $R_5$, and $R_7$ are as defined in lines X.001-X.032 in table X.

Table 22:

This table discloses the 32 compounds 22.001 to 22.032 of the formula (Iag):

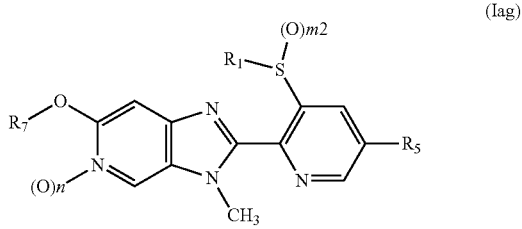

(Iag)

wherein n is 0, m2 is 0, and $R_1$, $R_5$, and $R_7$ are as defined in lines X.001-X.032 in table X. For example, compound 22.025 has the following structure:

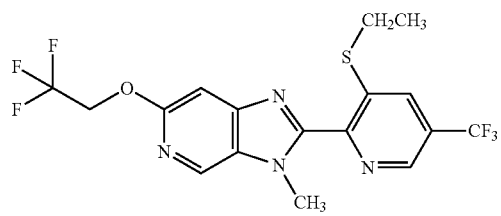

(22.025)

Table 23:

This table discloses the 32 compounds 23.001 to 123.032 of the formula (Iaa), wherein n is 0, m2 is 2, and $R_1$, $R_5$, and $R_7$ are as defined in lines X.001-X.032 in table X.

The compounds of formula I according to the invention are preventively and/or curatively valuable active ingredients in the field of pest control, even at low rates of application, which have a very favourable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate.

Examples of the abovementioned animal pests are:

from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*,

*Cerotoma* spp, *Conoderus* spp., *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. *and* Trogoderma spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotino-phara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp., *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera* Zehnter, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp, *Atta* spp., *Cephus* spp., *Diprion* spp., Diprionidae, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis* geminate from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Grapholita* spp., *Hedya nubiferana*, *Heliothis* spp., *Hellula undalis*, *Herpetogramma* spp., *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, Prays spp., *Pseudoplusia* spp., *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example,

*Calliothrips phaseoli*, *Frankliniella* spp., *Heliothrips* spp, *Hercinothrips* spp., *Parthenothrips* spp, *Scirtothrips aurantii*, *Sericothrips variabilis*, *Taeniothrips* spp., *Thrips* spp;

from the order Thysanura, for example, *Lepisma saccharine*.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis*, *Anthemis* spp., *Antirrhinum* spp., *Aster* spp., *Begonia* spp. (e.g. *B. elatior, B. semperflorens, B. tubéreux*), *Bougainvillea* spp., *Brachycome* spp., *Brassica* spp. (ornamental), *Calceolaria* spp., *Capsicum annuum*, *Catharanthus roseus*, *Canna* spp., *Centaurea* spp., *Chrysanthemum* spp., *Cineraria* spp. (*C. maritime*), *Coreopsis* spp., *Crassula coccinea*, *Cuphea ignea*, *Dahlia* spp., *Delphinium* spp., *Dicentra spectabilis*, *Dorotheantus* spp., *Eustoma grandiflorum*, *Forsythia* spp., *Fuchsia* spp., *Geranium gnaphalium*, *Gerbera* spp., *Gomphrena globose*, *Heliotropium* spp., *Helianthus* spp., *Hibiscus* spp., *Hortensia* spp., *Hydrangea* spp., *Hypoestes phyllostachya*, *Impatiens* spp. (*I. Walleriana*), *Iresines* spp., *Kalanchoe* spp., *Lantana camara*, *Lavatera trimestris*, *Leonotis leonurus*, *Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonate*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola*, *Schizanthus wisetonensis*, *Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium*, *Apium graveolus*, *Asparagus officinalis*, *Beta vulgarus*, *Brassica* spp. (*B. Oleracea, B. Pekinensis, B. rapa*), *Capsicum annuum*, *Cicer arietinum*, *Cichorium endivia*, *Cichorum* spp. (*C. intybus, C. endivia*), *Citrillus lanatus*, *Cucumis* spp. (*C. sativus, C. melo*), *Cucurbita* spp. (*C. pepo, C. maxima*), *Cyanara* spp. (*C. scolymus, C. cardunculus*), *Daucus carota*, *Foeniculum vulgare*, *Hypericum* spp., *Lactuca sativa*, *Lycopersicon* spp. (*L. esculentum, L. lycopersicum*), *Mentha* spp., *Ocimum basilicum*, *Petroselinum crispum*, *Phaseolus* spp. (*P. vulgaris, P. coccineus*), *Pisum sativum*, *Raphanus sativus*, *Rheum rhaponticum*, *Rosemarinus* spp., *Salvia* spp., *Scorzonera hispanica*, *Solanum melongena*, *Spinacea oleracea*, *Valerianella* spp. (*V. locusta, V. eriocarpa*) and *Vicia faba*.

Preferred ornamental species include African violet, Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia, rosemary, sage, St. Johnswort, mint, sweet pepper, tomato and cucumber.

The active ingredients according to the invention are especially suitable for controlling *Aphis craccivora*, *Diabrotica balteata*, *Heliothis virescens*, *Myzus persicae*, *Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla*, *Meloidogyne incognita*, *Meloidogyne javanica*, *Meloidogyne arenaria* and other *Meloidogyne* species; cyst-forming nematodes, *Globodera rostochiensis* and other *Globodera* species; *Heterodera avenae*, *Heterodera glycines*, *Heterodera schachtii*, *Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor*, *Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus*, *Pratylenchus penetrans*, *Pratylenchus curvitatus*, *Pratylenchus goodeyi* and other *Pratylenchus* species; Burrowing nematodes, *Radopholus similis* and other *Radopholus* species; Reniform nematodes, *Rotylenchus robustus*, *Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni*, *Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. Nemoralis*); ochlodina; *Deroceras* (*D. agrestis, D. empiricorum, D. laeve, D. reticulatum*); *Discus* (*D. rotundatus*); *Euomphalia*; *Galba* (*G. trunculata*); *Helicelia* (*H. itala, H. obvia*); Helicidae *Helicigona arbustorum*); Helicodiscus; *Helix* (*H. aperta*); *Limax* (*L. cinereoniger, L. flavus, L. marginatus, L. maximus, L. tenellus*); *Lymnaea*; *Milax* (*M. gagates, M. marginatus, M. sowerbyi*); *Opeas*; *Pomacea* (*P. canaticulata*); *Vallonia* and *Zanitoides*.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch). The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium, Anthracnose*, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents. A further object of the invention is therefore a substrate selected from nonwoven and fabric material comprising a composition which contains a compound of formula I.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO 2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, |

TABLE B-continued

Examples of native woodborers of economic importance.

| Family | Species | Host or Crop Infested |
|---|---|---|
| | | Peach, Persimmon, Plum, Poplar, Quince, Redbud, Serviceberry, Sycamore, Walnut, Willow |
| | Texania campestris | Basswood, Beech, Maple, Oak, Sycamore, Willow, Yellow-poplar |
| Cerambycidae | Goes pulverulentus | Beech, Elm, Nuttall, Willow, Black oak, Cherrybark oak, Water oak, Sycamore |
| | Goes tigrinus | Oak |
| | Neoclytus acuminatus | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | Neoptychodes trilineatus | Fig, Alder, Mulberry, Willow, Netleaf hackberry |
| | Oberea ocellata | Sumac, Apple, Peach, Plum, Pear, Currant, Blackberry |
| | Oberea tripunctata | Dogwood, Viburnum, Elm, Sourwood, Blueberry, Rhododendron, Azalea, Laurel, Poplar, Willow, Mulberry |
| | Oncideres cingulata | Hickory, Pecan, Persimmon, Elm, Sourwood, Basswood, Honeylocust, Dogwood, Eucalyptus, Oak, Hackberry, Maple, Fruit trees |
| | Saperda calcarata | Poplar |
| | Strophiona nitens | Chestnut, Oak, Hickory, Walnut, Beech, Maple |
| Scolytidae | Corthylus columbianus | Maple, Oak, Yellow-poplar, Beech, Boxelder, Sycamore, Birch, Basswood, Chestnut, Elm |
| | Dendroctonus frontalis | Pine |
| | Dryocoetes betulae | Birch, Sweetgum, Wild cherry, Beech, Pear |
| | Monarthrum fasciatum | Oak, Maple, Birch, Chestnut, Sweetgum, Blackgum, Poplar, Hickory, Mimosa, Apple, Peach, Pine |
| | Phloeotribus liminaris | Peach, Cherry, Plum, Black cherry, Elm, Mulberry, Mountain-ash |
| | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as Cyclocephala spp. (e.g. masked chafer, C. lurida), Rhizotrogus spp. (e.g. European chafer, R. majalis), Cotinus spp. (e.g. Green June beetle, C. nitida), Popillia spp. (e.g. Japanese beetle, P. japonica), Phyllophaga spp. (e.g. May/June beetle), Ataenius spp. (e.g. Black turfgrass ataenius, A. spretulus), Maladera spp. (e.g. Asiatic garden beetle, M. castanea) and Tomarus spp.), ground pearls (Margarodes spp.), mole crickets (tawny, southern, and short-winged; Scapteriscus spp., Gryllotalpa africana) and leatherjackets (European crane fly, Tipula spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and green bugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattelagermanica* and *Supella* spp.

Of the subclass Acaria (Acarida) and the orders Meta- and Meso-*stigmata*, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus*, *Chlorophorus pilosis*, *Anobium punctatum*, *Xestobium rufovillosum*, *Ptilinuspecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthesrugicollis*, *Xyleborus* spec., *Tryptodendron* spec., *Apate monachus*, *Bostrychus capucins*, *Heterobostrychus brunneus*, *Sinoxylon* spec. and *Dinoderus minutus*, and also hymenopterans such as *Sirex juvencus*, *Urocerus gigas*, *Urocerus gigas taignus* and *Urocerus augur*, and termites such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl-hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| Wettable powders | a) | b) | c) |
| --- | --- | --- | --- |
| active ingredients | 25% | 50% | 75% |
| sodium lignosulfonate | 5% | 5% | — |

| Wettable powders | a) | b) | c) |
| --- | --- | --- | --- |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
| --- | --- | --- | --- |
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
| --- | --- |
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
| --- | --- | --- | --- |
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
| --- | --- |
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
| --- | --- |
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| | |
| --- | --- |
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
| --- | --- |
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mpt" means melting point in ° C. Free radicals represent methyl groups. $^1$H NMR measurements were recorded on a Brucker 400 MHz spectrometer, chemical shifts are given in ppm relevant to a TMS standard. Spectra measured in deuterated solvents as indicated.
LCMS Methods:
Method 1:
Spectra were recorded on a Mass Spectrometer from Waters (SQD, SQDII or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 mm, 30×2.1 mm, Temp: 60° C., DAD Wavelength range (nm): 210 to 500, Solvent Gradient: A=water+5% MeOH+ 0.05% HCOOH, B=Acetonitrile+0.05% HCOOH, gradient: 10-100% B in 1.2 min; Flow (ml/min) 0.85.

PREPARATIVE EXAMPLES

Example P1: 2-[3-ethylsulfonyl-5-(trifluoromethyl)-2-pyridyl]-3-methyl-6-(trifluoromethylsulfanyl) imidazo[4,5-c]pyridine (Compound P10, Table P)

(Compound P10)

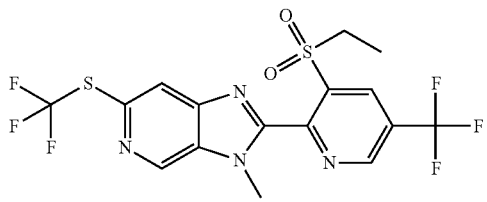

Step A: 2-bromo-5-fluoro-1-oxido-pyridin-1-ium

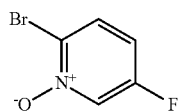

To a stirred solution of 2-bromo-5-fluoropyridine (5.0 g, 28.4 mmol) in TFA (10.0 mL) was added H$_2$O$_2$ (30%, 15 mL) dropwise at 0° C., the mixture was stirred under reflux overnight. After cooling, the reaction system was poured onto ice-water, extracted with dichloromethane/methanol (10:1, 50 mL×3), the organic layer was washed with saturated sodium bicarbonate solution and brine, and dried over anhydrous sodium sulfate. After filtration and concentration in vacuo, the crude product was used in the next step without further purification.

Step B: 2-bromo-5-fluoro-4-nitro-1-oxido-pyridin-1-ium

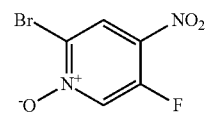

To a solution of 2-bromo-5-fluoro-1-oxido-pyridin-1-ium (4.6 g, 23.9 mmol) in sulfuric acid (conc.) (20 mL) was added fuming nitric acid (10 mL) slowly at 0° C. After the addition, the reaction temperature was raised to 120° C., and stirring continued at this temperature for 4 h. After cooling to room temperature, the reaction solution was poured onto ice-water. The pH value was adjusted to 1 with NH$_4$OH. The precipitate was filtered and oven dried to afford the title compound as light yellow solid.

Step C: 6-bromo-N-methyl-4-nitro-1-oxido-pyridin-1-ium-3-amine

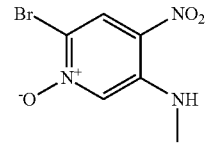

To a solution of 2-bromo-5-fluoro-4-nitro-1-oxido-pyridin-1-ium (1.1 g, 4.6 mmol) in ethanol (10 mL) was added MeNH$_2$/ethanol (4 mL). The reaction mixture was stirred at room temperature for 4 h. The mixture was concentrated in vacuo to give the title compound as a solid which was used for the next step without further purification.

Step D: 6-bromo-N-methyl-4-nitro-pyridin-3-amine

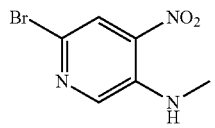

To a solution of 6-bromo-N-methyl-4-nitro-1-oxido-pyridin-1-ium-3-amine (crude from above, 4.6 mmol) in dichloromethane (10 mL) was added PBr$_3$ (1.0 mL). The reaction mixture was stirred at ambient temperature for 1 hour. The mixture was dried under vacuum to give the title compound as a jacinth solid and used for the next step without further purification.

Step E: 6-bromo-N3-methyl-pyridine-3,4-diamine

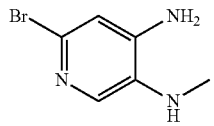

To a solution of 6-bromo-N-methyl-4-nitro-pyridin-3-amine (crude, 4.6 mmol) in methanol (10 mL) was added Raney Ni (20% wt), and hydrazine hydrate (1.0 mL) was added dropwise at 0° C. The reaction mixture was stirred at room temperature for a few minutes. Raney Ni was filtered off through celite; the filtrate was dried in vacuo and purified with chromatography column on silica gel (dichloromethane:methanol, 10:1) to afford the title compound as a light purple solid. Mpt. 156-158° C.

LCMS (standard method 1): 0.61 min, 202/204 (M+H).
$^1$H NMR (400 MHz, DMSO-$d_6$): δ(ppm) 7.20 (s, 1H), 6.65 (s, 1H), 6.54 (brs, 2H), 3.34 (s, 1H), 2.69 (d, J=6.4 Hz, 3H).

Step F: N-(4-amino-6-bromo-3-pyridyl)-3-ethylsulfonyl-N-methyl-5-(trifluoromethyl)pyridine-2-carboxamide

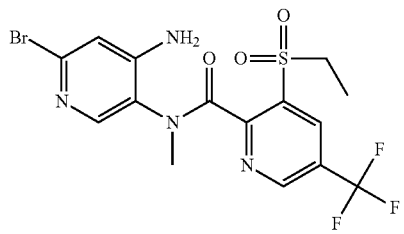 [SMILES: CCS(=O)(=O)c1cc(C(F)(F)F)cnc1C(=O)N(C)c1cnc(Br)cc1N]

To a stirred solution of 6-bromo-N3-methyl-pyridine-3,4-diamine (0.60 g, 2.96 mmol), 3-ethylsulfonyl-5-(trifluoromethyl)pyridine-2-carboxylic acid (0.92 g, 3.26 mmol, prepared as in WO 2013180194) and HATU (1.4 g, 3.68 mmol) in DMF (5.0 mL) was added DIPEA (1.2 ml, 7.26 mmol). The system was stirred at room temperature overnight. The reaction was diluted with EtOAc and H$_2$O, the organic layer was washed with brine and water, and dried over anhydrous sodium sulfate. After filtration and concentration in vacuo, the crude title product was used for the next step without further purification.

Step G: 6-bromo-2-[3-ethylsulfonyl-5-(trifluoromethyl)-2-pyridyl]-3-methyl-imidazo[4,5-c]pyridine

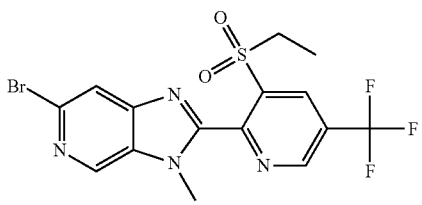 [SMILES: CCS(=O)(=O)c1cc(C(F)(F)F)cnc1-c1nc2cc(Br)ncc2n1C]

A solution of N-(4-amino-6-bromo-3-pyridyl)-3-ethylsulfonyl-N-methyl-5-(trifluoromethyl)pyridine-2-carboxamide (crude, 2.96 mmol) in acetic acid (5.0 mL) was stirred at 120° C. overnight. The mixture was evaporated to dryness. The residue was purified by chromatography on silica gel (Petroleum ether:EtOAc=4:1) to afford the title compound as white solid. $^1$H NMR (400 MHz, DMSO-$d_6$): δ (ppm) 9.53 (s, 1H), 8.94 (s, 1H), 8.74 (s, 1H), 8.01 (s, 1H), 3.83 (q, J=7.6 Hz, 2H), 3.79 (s, 3H), 1.19 (t, J=7.2 Hz, 3H). $^{19}$F NMR (300 MHz, DMSO-d6): δ (ppm) −60.42 (s, 3F). ESI-MS (+): 449 (M+H), 472 (M+Na); ESI-MS (−): 447 (M−H). Mpt. 188-190° C. LCMS (standard method 1): Rt. 0.95 min, 449/451 (M+H).

Step H: 2-[3-ethylsulfonyl-5-(trifluoromethyl)-2-pyridyl]-3-methyl-6-(trifluoromethylsulfanyl)imidazo[4,5-c]pyridine (Compound P10, Table P)

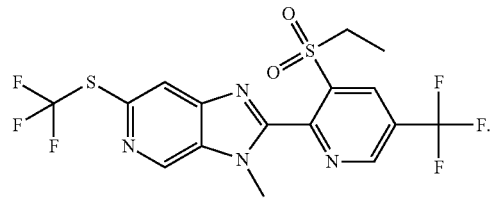

(Compound P10, Table P)

In a glove box, CuF$_2$ (5.1 g, 50 mmol), S$_8$ (1.6 g, 50 mmol), and 100 mL CH$_3$CN were added to an oven-dried resealable Schlenk tube possessing a Teflon screw valve. CF$_3$SiMe$_3$ (21.3 g, 150 mmol) was added into this tube and the tube was sealed. The reaction mixture was stirred in a pre-heated oil bath at 90° C. for 24 h. The reaction mixture was then allowed to cool to room temperature and filtered through Celite. The volatiles were removed under reduced pressure and the resulting dark-brown solid was washed with Et$_2$O (3×30 mL). The solid was re-dissolved in 40 mL of CH$_3$CN and 2,2'-bipyridine (7.8 g, 50 mmol) in 100 mL of Et$_2$O was added to this solution. The resulting solution was stirred at room temperature for 2 h, and then kept at −25° C. for 48 h. The resulting red crystals were washed with diethyl ether (2×40 mL), and dried under reduced pressure to give (bpy)CuSCF$_3$.

A solution of (bpy)CuSCF$_3$ (8.2 g, 25.6 mmol) and 6-bromo-2-[3-ethylsulfonyl-5-(trifluoromethyl)-2-pyridyl]-3-methyl-imidazo[4,5-c]pyridine (4 g, 8.9 mmol) in 120 ml of CH$_3$CN was refluxed for 24 h under nitrogen. The reaction mixture was removed from the oil bath and allowed to cool, filtered through SiO$_2$, eluting with diethyl ether. The ether filtrate was washed with brine, and concentrated in vacuo. The residue was purified by silica gel column chromatography to give the title compound as a white solid. Mpt. 180-181° C.

LCMS (standard method 1): 1.04 min, 471 (M+H). $^1$H NMR (600 MHz, CDCl$_3$): δ ppm 1.42 (t, J=7.5 Hz, 3H), 3.91 (q, J=7.5 Hz, 2H), 3.98 (s, 3H), 8.56 (s, 1H), 8.80 (d, J=2.1 Hz, 1H), 9.02 (s, 1H), 9.27 (d, J=1.8 Hz, 1H); $^{13}$C NMR (151 MHz, CDCl$_3$): δ ppm 7.0 (s, 1C), 32.1 (s, 1C), 52.0 (s, 1C), 114.1 (s, 1C), 122.1 (q, J=272 Hz, 1C), 124.9 (q, J=338 Hz, 1C), 128.4 (q, J=35 Hz, 1C), 134.6 (s, 1C), 135.3 (s, 1C), 137.3 (q, J=4 Hz, 1C), 138.4 (s, 1C), 148.0 (s, 1C), 149.5 (q, J=2 Hz, 1C), 149.7 (q, J=3 Hz, 1C), 151.4 (s, 1C), 152.5 (s, 1C); $^{19}$F NMR (400 MHz, CDCl$_3$): δ ppm −36.9 (s, 3F), −58.1 (s, 3F).

Example P2: 2-[3-Ethylsulfanyl-5-(trifluoromethyl)-2-pyridyl]-3-methyl-6-(trifluoromethylsulfanyl) imidazo[4,5-c]pyridine (Compound P11, Table P)

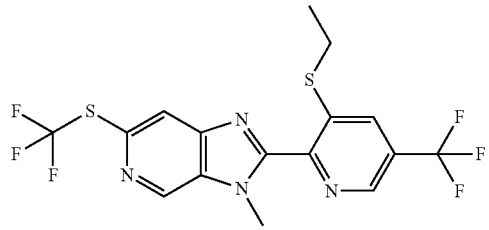

(Compound P11, Table P)

Step A: N-[2-Bromo-5-(methylamino)-4-pyridyl]-3-ethylsulfanyl-5-(trifluoromethyl)pyridine-2-carboxamide

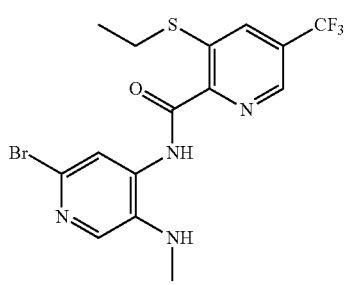 [SMILES: CCSc1cc(C(F)(F)F)cnc1C(=O)Nc1cc(Br)ncc1NC]

To a solution of 3-ethylsulfanyl-5-(trifluoromethyl)pyridine-2-carboxylic acid (4.68 g, 18.6 mmol, prepared as described in WO 2014 104407) in 5 ml DMF was added 6-bromo-N3-methyl-pyridine-3,4-diamine (3.42 g, 16.9 mmol, prepared as described in step E, example P1), [O-(7-Azabenzotriazol-1-yl)-N,N, N',N'-tetramethyluronium-hexafluorphosphate](HATU, 8.06 gg, 21.0 mmol) and di-isopropylethyl amine (5.36 g, 41.5 mmol, 7.10 ml) at 0° C. The orange suspension was allowed to warm to rt and stirred over night. LCMS analysis after this time showed reaction completion. The now orange solution was diluted with EtOAc and water. The organic phase was separated and the aqueous phase back extracted with EtOAc, and the combined organic phases dried over Na2SO4, filtered and concentrated in vacuo. The crude product was purified on a Torrent machine with a 330 g Redisep silica gel cartridge, eluting with cyclohexane:EtOAc gradient 0:100% to give the title compound as a white solid.

LCMS (standard method 1): Rt. 1.30 min, 435/437 (M+H). $^1$H NMR (400 MHz, CHLOROFORM-d) δ ppm: 1.37 (t, J=7.34 Hz, 3H); 2.97-3.07; (m, 2H); 3.26-3.41 (s, 3H); 4.60-4.75 (m, 2H); 6.71 (s, 1H); 7.73 (d, J=1.47 Hz, 1H); 7.95 (s, 1H); 8.35 (d, J=0.73 Hz, 1H).

Step B: 6-Bromo-2-[3-ethylsulfanyl-5-(trifluoromethyl)-2-pyridyl]-3-methyl-imidazo[4,5-c]pyridine

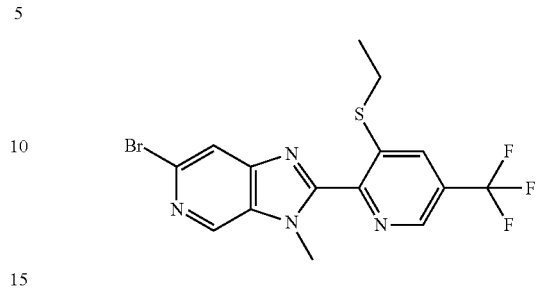

A solution of N-[2-bromo-5-(methylamino)-4-pyridyl]-3-ethylsulfanyl-5-(trifluoromethyl)pyridine-2-carboxamide (7.90 g, 18.1 mmol) in acetic acid (30 ml) was heated at 120° C. for 12 hr at which time LCMS analysis showed reaction completion. The solvent was removed in vacuo and the crude product purified on a Torrent machine with a 220 g Redisep silica gel cartridge, eluting with cyclohexane:EtOAc gradient 0:100% to give the title compound as a white solid.

LCMS (standard method 1): Rt. 0.95 min, 417/419 (M+H). $^1$H NMR (400 MHz, CHLOROFORM-d) δ ppm; 1.39 (t, J=7.34 Hz, 3H); 3.02 (q, J=7.34 Hz, 2H); 4.03 (s, 3H): 7.93 (d, J=0.73 Hz, 1H); 7.99 (d, J=1.10 Hz, 1H); 8.68 (d, J=1.10 Hz, 1H); 8.74 (d, J=0.73 Hz, 1H).

Step C: 2-[3-Ethylsulfanyl-5-(trifluoromethyl)-2-pyridyl]-3-methyl-6-(trifluoromethylsulfanyl)imidazo[4,5-c]pyridine (Compound P11, Table P)

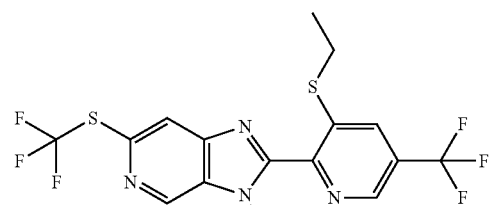

(Compound P11)

A solution of (bpy)CuSCF3 (480 mg, 1.5 mmol) and 6-bromo-2-[3-ethylsulfanyl-5-(trifluoromethyl)-2-pyridyl]-3-methyl-imidazo[4,5-c]pyridine (209 mg, 0.5 mmol) in 15 ml of CH3CN was refluxed for 24 h under nitrogen. The reaction mixture was removed from the oil bath and allowed to cool and then filtered through SiO2, eluted with diethyl ether, washed with brine, and concentrated in vacuo. The residue was purified by silica gel column chromatography to give the title compound as a beige powder. Mpt. 147-148° C.

LCMS (standard method 1): Rt. 1.11 min, 439 (M+H). $^1$H NMR (400 MHz, CDCl3): δ ppm 1.40 (t, J=6.8 Hz, 3H); 3.02 (q, J=7.2 Hz, 2H); 4.09 (s, 3H); 7.94 (s, 1H); 8.23 (s, 1H); 8.75 (s, 1H); 8.96 (s, 1H); $^{19}$F NMR (300 MHz, CDCl3): δ ppm −58.6 (s, 3F); −79.5 (s, 3F).

Example P3: 2-[3-ethylsulfonyl-5-(trifluoromethyl)-2-pyridyl]-3-methyl-6-(trifluoromethylsulfonyl) imidazo[4,5-c]pyridine (Compound P8, Table P)

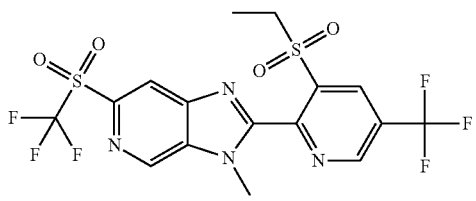

(Compound P8, Table P)

A solution of 2-[3-Ethylsulfonyl-5-(trifluoromethyl)-2-pyridyl]-3-methyl-6-(trifluoromethylsulfanyl) imidazo[4,5-c]pyridine (507 mg, 1.08 mmol), $NaWO_4.2H_2O$ (330 mg, 1 mmol) and 8 ml 30% $H_2O_2$ in 40 ml of $CH_3CN$ was refluxed for 48 hr. The reaction mixture was removed from the oil bath and allowed to cool, then poured into a saturated solution of $Na_2S_2O_3$ in water, and extracted with ethyl acetate three times. The combined organic layers were dried over sodium sulfate, filtered and concentrated in vacuo. The crude product was purified by column chromatography on silica gel to give the title product as a white powder. Mpt. 210-212° C.

LCMS (standard method 1): Rt. 1.02 min, 503 (M+H). $^1$H NMR (600 MHz, $CDCl_3$): δ ppm 1.43 (t, J=7.4 Hz, 3H), 3.88 (q, J=7.4 Hz, 2H), 4.01 (s, 3H), 8.72 (s, 1H), 8.80 (d, J=1.9 Hz, 1H), 9.15 (s, 1H), 9.28 (dq, J=1.9, 0.7 Hz, 1H); $^{13}$C NMR (151 MHz, $CDCl_3$): δ ppm 7.1 (s, 1C), 32.3 (s, 1C), 52.0 (s, 1C), 120.0 (q, J=327 Hz, 1C), 122.1 (q, J=274 Hz, 1C), 120.1 (s, 1C), 128.6 (q, J=35 Hz, 1C), 135.5 (s, 1C), 136.3 (s, 1C), 137.3 (q, J=3 Hz, 1C), 138.5 (s, 1C), 143.4 (s, 1C), 147.2 (s, 1C), 149.8 (q, J=4 Hz, 1C), 150.9 (s, 1C), 153.5 (s, 1C); $^{19}$F NMR (400 MHz, $CDCl_3$): δ ppm −58.2 (s, 3F), −71.6 (s, 3F).

Example P4. 2-[3-ethylsulfonyl-5-(trifluoromethyl)-2-pyridyl]-3-methyl-6-(trifluoromethylsulfinyl) imidazo[4,5-c]pyridine (Compound P9, Table P)

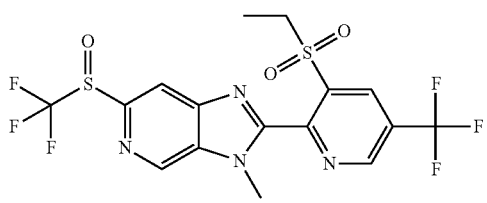

(Compound P9, Table P)

Compound 2-[3-Ethylsulfonyl-5-(trifluoromethyl)-2-pyridyl]-3-methyl-6-(trifluoromethylsulfanyl)imidazo[4,5-c]pyridine (540 mg, 1.15 mmol) and m-CPBA (1.49 g, 8.66 mmol) in 30 ml of $CH_2Cl_2$ was stirred at room temperature for 6 h. Then the mixture was poured into a saturated solution of $NaHCO_3$ and $Na_2SO_3$ in water, and extracted with ethyl acetate three times. The combined organic layers were dried over sodium sulfate, filtered and concentrated in vacuo. The crude product was purified by column chromatography on silica gel to give the title product as a white solid. Mpt. 206-207° C.

LCMS (standard method 1): Rt. 0.96 min, 487 (M+H). $^1$H NMR (600 MHz, $CDCl_3$): δ ppm 1.44 (t, J=7.4 Hz, 3H), 3.86 (s, 3H), 3.90 (q, J=7.5 Hz, 2H), 8.28 (s, 1H), 8.69 (s, 1H), 8.79 (d, J=1.8 Hz, 1H), 9.26 (dq, J=1.8, 0.6 Hz, 1H); $^{13}$C NMR (151 MHz, $CDCl_3$): δ ppm 7.1 (s, 1C), 32.5 (s, 1C), 52.0 (s, 1C), 117.0 (s, 1C), 122.1 (q, J=274 Hz, 1C), 123.9 (s, 1C), 128.5 (q, J=34 Hz, 1C), 136.2 (s, 1C), 137.5 (q, J=4 Hz, 1C), 138.4 (s, 1C), 140.0 (s, 1C), 143.7 (br. s., 1C), 149.7 (q, J=4 Hz, 1C), 150.5 (s, 1C), 153.2 (s, 1C); $^{19}$F NMR (400 MHz, $CDCl_3$): δ ppm −62.1 (s, 3F), −71.7 (s, 3F).

Example P5: 6-(difluoromethoxy)-2-[3-ethylsulfanyl-5-(trifluoromethyl)-2-pyridyl]-3-methyl-imidazo[4,5-c]pyridine (Compound P13, Table P)

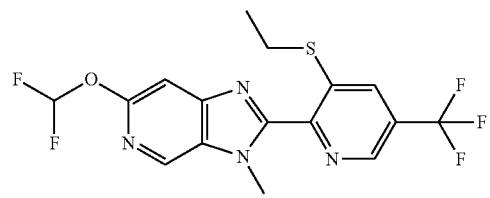

(compound P13, Table P)

Step A: 2-[3-ethylsulfanyl-5-(trifluoromethyl)-2-pyridyl]-3-methyl-imidazo[4,5-c]pyridin-6-ol

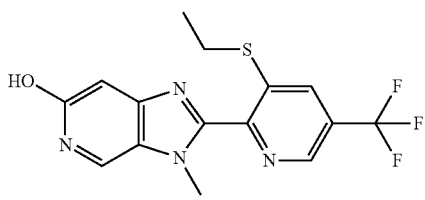 [SMILES: CCSc1cc(C(F)(F)F)cnc1-c1nc2cc(O)ncc2n1C]

A mixture of 6-Bromo-2-[3-ethylsulfanyl-5-(trifluoromethyl)-2-pyridyl]-3-methyl-imidazo[4,5-c]pyridine: (3 g, 7.2 mmol), $K_3PO_4$ (2.29 g, 10.8 mmol), CuI (274 mg, 1.44 mmol) and N,N'-dimethyl-1,2-ethylenediamine (630 mg, 7.2 mmol) in 40 ml of $H_2O$ was refluxed at 120° C. for 6 h under nitrogen. The reaction mixture was then allowed to cool to room temperature and extracted with ethyl acetate three times. The combined organic layers were dried over sodium sulfate, filtered and concentrated under vacuum. The residue was purified by column chromatography on silica gel to give the title compound as a white powder. $^1$HNMR (400 MHz, DMSO-$d_6$): δ ppm 1.20 (t, 3H), 3.12 (q, 2H), 3.81 (s, 3H), 6.72 (s, 1H), 8.27 (s, 1H), 8.46 (s, 1H), 8.91 (s, 1H), 10.58 (bs, 1H); $^{19}$FNMR (376 MHz, DMSO-$d_6$): δ ppm −56.2 (s, 3F); ESI-MS (+):355 (M+H)$^+$.

Step B: 6-(difluoromethoxy)-2-[3-ethylsulfanyl-5-(trifluoromethyl)-2-pyridyl]-3-methyl-imidazo[4,5-c]pyridine (Compound P13, Table P)

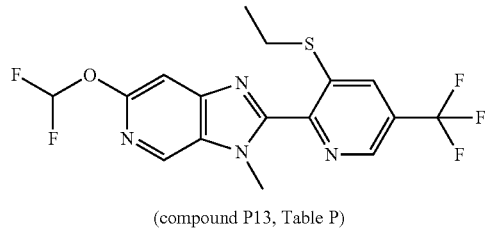 [SMILES: CCSc1cc(C(F)(F)F)cnc1-c1nc2cc(OC(F)F)ncc2n1C]

(compound P13, Table P)

A suspension of 2-[3-ethylsulfanyl-5-(trifluoromethyl)-2-pyridyl]-3-methyl-imidazo[4,5-c]pyridin-6-ol (300 mg, 0.85 mmol) and $Cs_2CO_3$ (1.52 g, 4.66 mmol) in 25 ml of DMF was stirred at 60° C. for 10 min, $CHF_2Cl$ gas was introduced to the mixture for 1 h. Then, the reaction mixture was poured into water and extracted with ethyl acetate three times. The combined organic layers were dried over sodium sulfate, filtered and concentrated under vacuum. The residue was purified by column chromatography on silica gel to give the title product as a white solid. $^1$HNMR (400 MHz, $CDCl_3$): δ ppm 1.39 (t, 3H), 3.0 (q, 2H), 4.01 (s, 3H), 7.28-7.65 (t, 1H), 7.37 (s, 1H), 7.93 (s, 1H), 8.48 (s, 1H), 8.74 (s, 1H); $^{19}$FNMR (376 MHz, $CDCl_3$): δ ppm −62.64 (s, 3F), −87 (d, 2F); ESI-MS (+): 405 (M+H)$^+$.

Example P6: 6-(difluoromethoxy)-2-[3-ethylsulfonyl-5-(trifluoromethyl)-2-pyridyl]-3-methyl-imidazo[4,5-c]pyridine (Compound, P6, Table P)

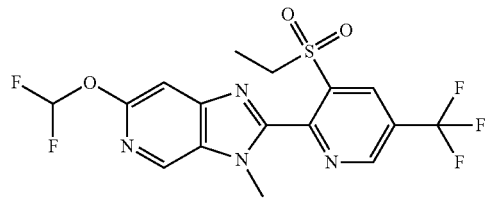

(Compound, P6, Table P)

A solution of 6-(difluoromethoxy)-2-[3-ethylsulfanyl-5-(trifluoromethyl)-2-pyridyl]-3-methyl-imidazo[4,5-c]pyridine (80 mg, 0.2 mmol) and m-CPBA (172 mg, 1 mmol) in 15 ml of DCM was stirred at room temperature for 2 h. Then, the mixture was poured into a saturated solution of $NaHCO_3$ and $Na_2SO_3$ in water and extracted with dichloromethane three times. The combined organic layers were dried over sodium sulfate, filtered and concentrated under vacuum. The residue was purified by column chromatography on silica gel to give the title product as a white solid. Mpt. 172-174° C.

LCMS (standard method 1): Rt. 0.98 min, 452 (M+H). $^1$HNMR (400 MHz, $CDCl_3$): δ ppm 1.39 (t, 3H), 3.85 (s, 3H), 3.89 (q, 2H), 7.3-7.66 (t, 1H), 7.27 (s, 1H), 8.52 (s, 1H), 8.77 (s, 1H), 9.24 (s, 1H); $^{19}$FNMR (376 MHz, $CDCl_3$): δ ppm −62.25 (s, 3F), −87.33 (d, 2F); ESI-MS (+): 437 (M+H)$^+$, 459 (M+Na)$^+$.

Example P7: 6 6-[bromo(difluoro)methoxy]-2-[3-ethylsulfonyl-5-(trifluoromethyl)-2-pyridyl]-3-methyl-imidazo[4,5-c]pyridine (Compound P5, Table P)

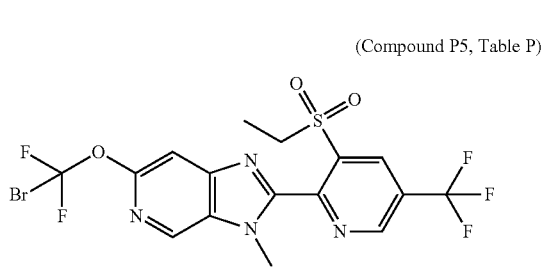 [SMILES: CCS(=O)(=O)c1cc(C(F)(F)F)cnc1-c1nc2cc(OC(F)(F)Br)ncc2n1C]

(Compound P5, Table P)

To a solution of 2-[3-ethylsulfanyl-5-(trifluoromethyl)-2-pyridyl]-3-methyl-imidazo[4,5-c]pyridin-6-ol (1.2 g, 3.4 mmol) in 30 mL of DMF at 0° C. was added 60% NaH (500 mg, 12.5 mmol) under an nitrogen atmosphere. After stirring at room temperature for 1 h the mixture was then heated to 60° C. for 30 min. A solution of $CF_2Br_2$ in dry DMF (17 ml, 1 mol/L) was then slowly added at 0° C. The reaction mixture was then stirred at room temperature for another 2 h, After this time, t-BuOK (420 mg, 3.74 mmol) was added. The reaction and the reaction mixture was stirred at 70° C. overnight. The mixture was poured into water and extracted with ethyl acetate three times. The combined organic layers were dried over sodium sulfate, filtered and concentrated under vacuum. The residue was purified by column chromatography on silica gel. The crude product of 6-[bromo(difluoro)methoxy]-2-[3-ethylsulfanyl-5-(trifluoromethyl)-2-pyridyl]-3-methyl-imidazo[4,5-c]pyridine (150 mg) and m-CPBA (470 mg, 2.73 mmol) in 25 ml of dichloromethane was stirred at room temperature for 2 h. Then the mixture was poured into a saturated solution of $NaHCO_3$ and $Na_2SO_3$ in water, and extracted with dichloromethane three times. The combined organic layers were dried over sodium sulfate, filtered and concentrated under vacuum. The residue was purified by preparative HPLC to give the title product 6-[bromo(difluoro)methoxy]-2-[3-ethylsulfonyl-5-(trifluoromethyl)-2-pyridyl]-3-methyl-imidazo[4,5-c]pyridine. Mpt. 164-165° C.

LCMS (standard method 1): Rt. 2.05 min, 515/517 (M+H). $^1$HNMR (400 MHz, $CDCl_3$): δ ppm 1.41 (t, 3H), 3.89 (m, 5H), 7.50 (s, 1H), 8.70 (s, 1H), 8.78 (s, 1H), 9.25 (s, 1H); $^{19}$FNMR (376 MHz, $CDCl_3$): δ ppm −62.40 (s, 3F), −15.49 (s, 2F).

Example P8: 2-[3-Ethylsulfonyl-5-(trifluoromethyl)-2-pyridyl]-3-methyl-6-(2,2,2-trifluoroethylsulfanyl)imidazo[4,5-c]pyridine (Compound P17, Table P)

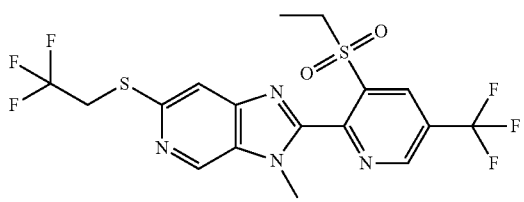 [SMILES: CCS(=O)(=O)c1cc(C(F)(F)F)cnc1-c1nc2cc(SCC(F)(F)F)ncc2n1C]

In a microwave vial 6-bromo-2-[3-ethylsulfonyl-5-(trifluoromethyl)-2-pyridyl]-3-methyl-imidazo[4,5-c]pyridine (0.50 g, 1.0 eq, 1.1 mmol), was dissolved in DMF (15 mL,). To this stirred solution 2,2,2-trifluoroethanethiol (0.19 g, 1.6 mmol) and copper(i) iodide (0.064 g, 0.30 eq, 0.33 mmol) were added. The reaction mixture was irradiated in the microwave oven at 130° C. for 1 h. LC/MS analysis showed the desired mass in ratio around 1:5. A further portion of 2,2,2-trifluoroethanethiol (C, 0.19 g, 0.15 mL, 1.4 eq, 1.6 mmol) and copper(i) iodide (0.064 g, 0.30 eq, 0.33 mmol) were added and the mixture was stirred at 130° C. for 2 h in the microwave. After this time the reaction mixture was diluted and extracted with ethyl acetate. The organic phase was washed with water and brine, dried over Na2SO4, filtered and concentrated in vacuo. The crude compound was purified over a silica gel cartridge (Rf200), eluting with cyclohexane:ethyl acetate to give the title compound as a yellowish solid.

$^1$H NMR (400 MHz, CHLOROFORM-d) δ ppm 1.39 (t, J=7.52 Hz, 3H) 3.86 (s, 3H) 3.86-3.93 (m, 2H) 4.02-4.13 (m, 2H) 7.70 (d, J=1.10 Hz, 1H) 8.76 (d, J=1.83 Hz, 1H) 8.82 (d, J=1.10 Hz, 1H) 9.23 (d, J=1.10 Hz, 1H)

LC-MS (Std-1) M+H (485); Rt=1.08 min

Example P9: 2-[3-Ethylsulfonyl-5-(trifluoromethyl)-2-pyridyl]-3-methyl-6-(2,2,2-trifluoroethylsulfinyl)imidazo[4,5-c]pyridine (Compound P15, Table P)

(compound P15, Table P)

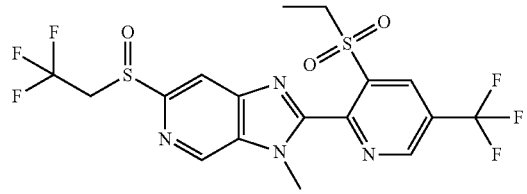

At 0° C. MCPBA (0.046 g, 1.0 eq, 0.21 mmol) was added to a solution of 2-[3-ethylsulfonyl-5-(trifluoromethyl)-2-pyridyl]-3-methyl-6-(2,2,2-trifluoroethylsulfanyl) imidazo[4,5-c]pyridine (a, 0.10 g, 1.0 eq, 0.21 mmol) in chloroform. After addition the ice-bath was kept for 10 min and then the milky solution was allowed to warm up to ambient temperature and stirred until reaction completion. The mixture was then quenched with saturated aqueous sodium thiosulfate aqueous solution, washed with saturated NaHCO3 (aq), dried over Na2SO4 and concentrated in vacuo.

Purification over a silica gel cartridge (Rf200) eluting with Cyclohexane/Ethyl acetate gave the title compound as a white solid.

$^1$H NMR (400 MHz, chloroform-d) δ ppm 1.41 (t, J=7.52 Hz, 3H) 3.47-3.59 (m, 1H) 3.87-3.94 (m, 2H) 3.96 (s, 3H) 4.05 (dd, J=14.31, 10.64 Hz, 1H) 8.47 (d, J=0.73 Hz, 1H) 8.78 (d, J=1.83 Hz, 1H) 8.96 (d, J=0.73 Hz, 1H) 9.26 (d, J=1.10 Hz, 1H)

LC/MS: Rt=0.95 Min; M+H[501]$^+$

TABLE P

Examples of compounds of formula (I) with physical and spectroscopic data:

| Comp. | STRUCTURE | RT (min) | [M + H] (measured) | Method | NMR | Mpt. ° C. |
|---|---|---|---|---|---|---|
| P1 | 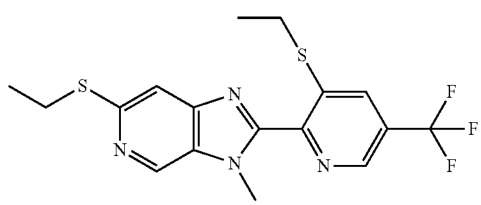 [SMILES: CCSc1cc2nc(-c3ncc(C(F)(F)F)cc3SCC)n(C)c2cn1] | 1.67 | 399 | Std-1 | | — |
| P2 | 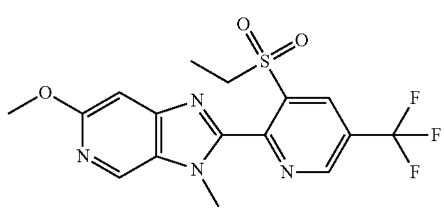 [SMILES: CCS(=O)(=O)c1cc(C(F)(F)F)cnc1-c1nc2cc(OC)ncc2n1C] | 0.87 | 401 | Std-1 | | 177-178 |
| P3 | 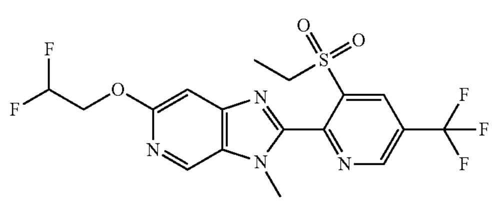 [SMILES: CCS(=O)(=O)c1cc(C(F)(F)F)cnc1-c1nc2cc(OCC(F)F)ncc2n1C] | 0.98 | 452 | Std-1 | | 172-174 |

TABLE P-continued

Examples of compounds of formula (I) with physical and spectroscopic data:

| Comp. | STRUCTURE | RT (min) | [M + H] (measured) | Method | NMR | Mpt. ° C. |
|---|---|---|---|---|---|---|
| P4 | 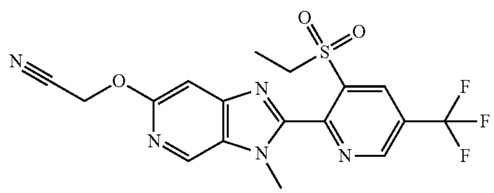 [SMILES: CCS(=O)(=O)c1cc(C(F)(F)F)cnc1-c1nc2cc(OCC#N)ncc2n1C] | 0.92 | 427 | Std-1 | | 198-200 |
| P5 | 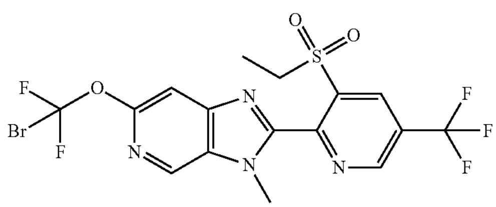 [SMILES: CCS(=O)(=O)c1cc(C(F)(F)F)cnc1-c1nc2cc(OC(F)(F)Br)ncc2n1C] | 2.05 | 515/517 | Std-1 | | 164-165 |
| P6 | 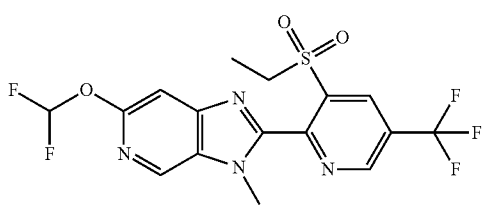 [SMILES: CCS(=O)(=O)c1cc(C(F)(F)F)cnc1-c1nc2cc(OC(F)F)ncc2n1C] | 0.99 | 437 | Std-1 | | 210-211 |
| P7 | 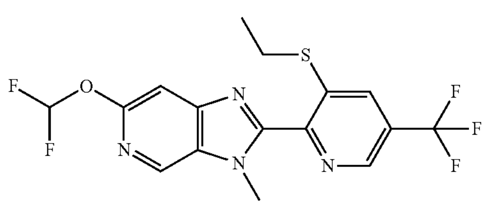 [SMILES: CCSc1cc(C(F)(F)F)cnc1-c1nc2cc(OC(F)F)ncc2n1C] | 1.06 | 405 | Std-1 | | 147-148 |
| P8 | 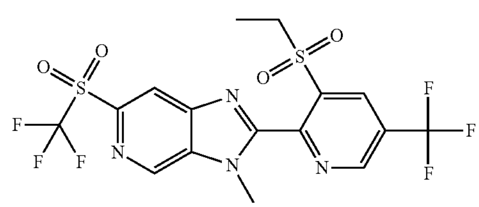 [SMILES: CCS(=O)(=O)c1cc(C(F)(F)F)cnc1-c1nc2cc(S(=O)(=O)C(F)(F)F)ncc2n1C] | 1.02 | 503 | Std-1 | | 210-212 |
| P9 | 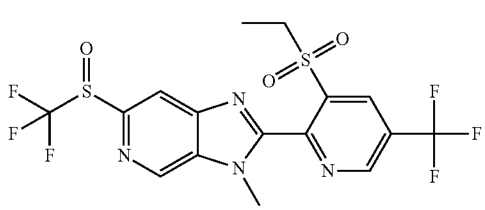 [SMILES: CCS(=O)(=O)c1cc(C(F)(F)F)cnc1-c1nc2cc(S(=O)C(F)(F)F)ncc2n1C] | 0.96 | 487 | Std-1 | | 206-207 |
| P10 | 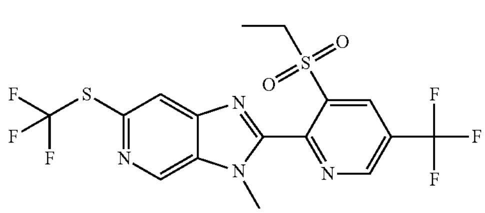 [SMILES: CCS(=O)(=O)c1cc(C(F)(F)F)cnc1-c1nc2cc(SC(F)(F)F)ncc2n1C] | 1.04 | 471 | Std-1 | | 180-181 |

TABLE P-continued

Examples of compounds of formula (I) with physical and spectroscopic data:

| Comp. | STRUCTURE | RT (min) | [M + H] (measured) | Method | NMR | Mpt. ° C. |
|---|---|---|---|---|---|---|
| P11 | 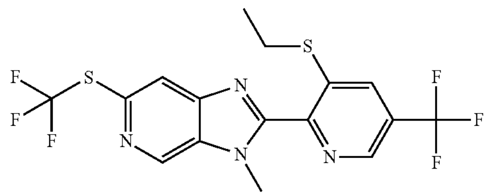 [SMILES: CCSc1cc(C(F)(F)F)cnc1-c1nc2cc(SC(F)(F)F)ncc2n1C] | 1.11 | 439 | Std-1 | | 147-148 |
| P12 | 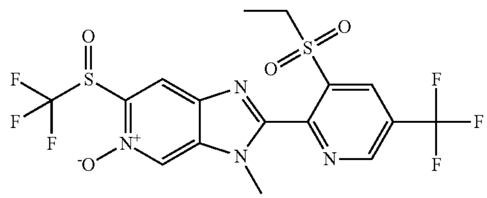 | 0.86 | 503 | Std-1 | | 234-235 |
| P13 | 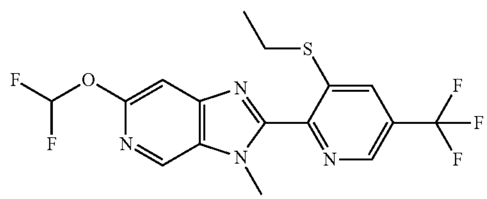 [SMILES: CCSc1cc(C(F)(F)F)cnc1-c1nc2cc(OC(F)F)ncc2n1C] | | | | $^1$HNMR (400 MHz, DMSO-$d_6$): δ ppm 1.20 (t, 3 H), 3.12 (q, 2 H), 3.81 (s, 3 H), 6.72 (s, 1 H), 8.27 (s, 1 H), 8.46 (s, 1 H), 8.91 (s, 1 H), 10.58 (bs, 1 H); | — |
| P14 | 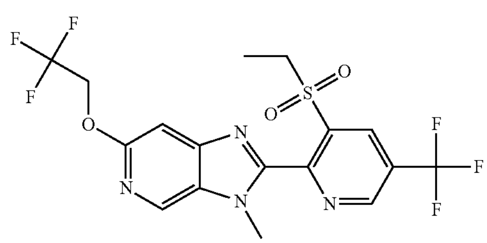 [SMILES: CCS(=O)(=O)c1cc(C(F)(F)F)cnc1-c1nc2cc(OCC(F)(F)F)ncc2n1C] | | | | | 125-126 |
| P15 | 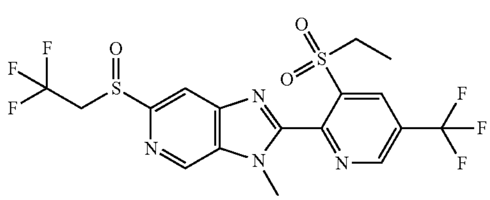 [SMILES: CCS(=O)(=O)c1cc(C(F)(F)F)cnc1-c1nc2cc(S(=O)CC(F)(F)F)ncc2n1C] | | | | | 204-205 |
| P16 | 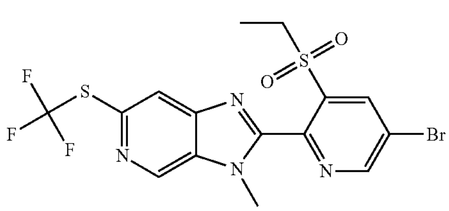 [SMILES: CCS(=O)(=O)c1cc(Br)cnc1-c1nc2cc(SC(F)(F)F)ncc2n1C] | 1.05 | 481/483 | Std-1 | | 159-160 |

TABLE P-continued

Examples of compounds of formula (I) with physical and spectroscopic data:

| Comp. | STRUCTURE | RT (min) | [M + H] (measured) | Method | NMR | Mpt. °C. |
|---|---|---|---|---|---|---|
| P17 | 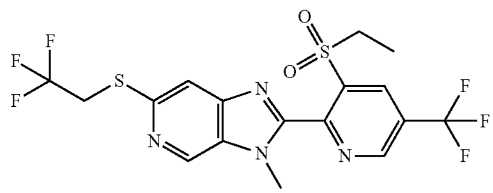 [SMILES: CCS(=O)(=O)c1cc(C(F)(F)F)cnc1-c1nc2cc(SCC(F)(F)F)ncc2n1C] | 1.08 | 485 | Std-1 | | — |

Further specific examples of compounds of the formula (I) are illustrated in the Tables 1 to 23 above.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1 to 23 and P of the present invention"):

An adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis (dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniartii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave* (742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa

[CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure $B_1$ (839)+TX, trimedlure $B_2$ (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, *Bacillus thuringiensis* delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin [CCN]+TX, jasmolin I (696)+TX, jasmolin II (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquinbutyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, fluxametamide (WO 2007/026965)+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium verrucaria* composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole [60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide [926914-55-8]+TX, flufiprole [704886-18-0]+TX, cyclaniliprole [1031756-98-5]+TX, tetraniliprole [1229654-66-3]+TX, guadipyr (described in WO2010/060231)+TX and cycloxaprid (described in WO 2005/077934)+TX; and microbials including: Acinetobacter lwoffii+TX, Acremonium alternatum+TX+TX, Acremonium cephalosporium+TX+TX, Acremonium diospyri+TX, Acremonium obclavatum+TX, Adoxophyes orana granulovirus (AdoxGV) (Capex®)+TX, Agrobacterium radiobacter strain K84 (Galltrol-A®)+TX, Alternaria alternate+TX, Alternaria cassia+TX, Alternaria destruens (Smolder®)+TX, Ampelomyces quisqualis (AQ10®)+TX, Aspergillus flavus AF36 (AF36®)+TX, Aspergillus flavus NRRL 21882 (Aflaguard®)+TX, Aspergillus spp.+TX, Aureobasidium pullulans+TX, Azospirillum+TX, (MicroAZ®+TX, TAZO B®)+TX, Azotobacter+TX, Azotobacter chroocuccum (Azotomeal®)+TX, Azotobacter cysts (Bionatural Blooming Blossoms®)+TX, Bacillus amyloliquefaciens+TX, Bacillus cereus+TX, Bacillus chitinosporus strain CM-1+TX, Bacillus chitinosporus strain AQ746+TX, Bacillus licheniformis strain HB-2 (Biostart™ Rhizoboost®)+TX, Bacillus licheniformis strain 3086 (EcoGuard®+TX, Green Releaf®)+TX, Bacillus circulans+TX, Bacillus firmus (BioSafe®, BioNem-WP®, VOTiVO®)+TX, Bacillus firmus strain I-1582+TX, Bacillus macerans+TX, Bacillus marismortui+TX, Bacillus megaterium+TX, Bacillus mycoides strain AQ726+TX, Bacillus papillae (Milky Spore Powder®)+TX, Bacillus pumilus spp.+TX, Bacillus pumilus strain GB34 (Yield Shield®)+TX, Bacillus pumilus strain AQ717+TX, Bacillus pumilus strain QST 2808 (Sonata®+TX, Ballad Plus®)+TX, Bacillus spahericus (VectoLe®)+TX, Bacillus spp.+TX, Bacillus spp. strain AQ175+TX, Bacillus spp. strain AQ177+TX, Bacillus spp. strain AQ178+TX, Bacillus subtilis strain QST 713 (CEASE®+TX, Serenade®+TX, Rhapsody®)+TX, Bacillus subtilis strain QST 714 (JAZZ®)+TX, Bacillus subtilis strain AQ153+TX, Bacillus subtilis strain AQ743+TX, Bacillus subtilis strain QST3002+TX, Bacillus subtilis strain QST3004+TX, Bacillus subtilis var. amyloliquefaciens strain FZB24 (Taegro®+TX, Rhizopro®)+TX, Bacillus thuringiensis Cry 2Ae+TX, Bacillus thuringiensis Cry1Ab+TX, Bacillus thuringiensis aizawai GC 91 (Agree®)+TX, Bacillus thuringiensis israelensis (BMP123®+TX, Aquabac®+TX, VectoBac®)+TX, Bacillus thuringiensis kurstaki (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, Bacillus thuringiensis kurstaki BMP 123 (Baritone®)+TX, Bacillus thuringiensis kurstaki HD-1 (Bioprotec-CAF/3P®)+TX, Bacillus thuringiensis strain BD#32+TX, Bacillus thuringiensis strain AQ52+TX, Bacillus thuringiensis var. aizawai (XenTari®+TX, DiPel®)+TX, bacteria spp. (GROWMEND®+TX, GROWSWEET®+TX, Shootup®)+TX, bacteriophage of Clavipacter michiganensis (AgriPhage®)+TX, Bakflor®+TX, Beauveria bassiana (Beaugenic®+TX, Brocaril WP®)+TX, Beauveria bassiana GHA (Mycotrol ES®+TX, Mycotrol O®+TX, BotaniGuard®)+TX, Beauveria brongniartii (Engerlingspilz®+TX, Schweizer Beauveria®+TX, Melocont®)+TX, Beauveria spp.+TX, Botrytis cineria+TX, Bradyrhizobium japonicum (TerraMax®)+TX, Brevibacillus brevis+TX, Bacillus thuringiensis tenebrionis (Novodor®)+TX, BtBooster+TX, Burkholderia cepacia (Deny®+TX, Intercept®+TX, Blue Circle®)+TX, Burkholderia gladii+TX, Burkholderia gladioli+TX, Burkholderia spp.+TX, Canadian thistle fungus (CBH Canadian Bioherbicide®)+TX, Candida butyri+TX, Candida famata+TX, Candida fructus+TX, Candida glabrata+TX, Candida guilliermondii+TX, Candida melibiosica+TX, Candida oleophila strain O+TX, Candida parapsilosis+TX, Candida pelliculosa+TX, Candida pulcherrima+TX, Candida reukaufii+TX, Candida saitoana (Bio-Coat®+TX, Biocure®)+TX, Candida sake+TX, Candida spp.+TX, Candida tenius+TX, Cedecea dravisae+TX, Cellulomonas flavigena+TX, Chaetomium cochliodes (Nova-Cide®)+TX, Chaetomium globosum (Nova-Cide®)+TX, Chromobacterium subtsugae strain PRAA4-1T (Grandevo®)+TX, Cladosporium cladosporioides+TX, Cladosporium oxysporum+TX, Cladosporium chlorocephalum+TX, Cladosporium spp.+TX, Cladosporium tenuissimum+TX, Clonostachys rosea (EndoFine®)+TX, Colletotrichum acutatum+TX, Coniothyrium minitans (Cotans WG®)+TX, Coniothyrium spp.+TX, Cryptococcus albidus (YIELDPLUS®)+TX, Cryptococcus humicola+TX, Cryptococcus infirmo-miniatus+TX, Cryptococcus laurentii+TX, Cryptphlebia leucotreta granulovirus (Cryptex®)+TX, Cupriavidus campinensis+TX, Cydia pomonella granulovirus (CYD-X®)+TX, Cydia pomonella granulovirus (Madex®+TX, Madex Plus®+TX, Madex Max/Carpovirusine®)+TX, Cylindrobasidium laeve (Stumpout®)+TX, Cylindrocladium+TX, Debaryomyces hansenii+TX, Drechslera hawaiinensis+TX, Enterobacter cloacae+TX, Enterobacteriaceae+TX, Entomophtora virulenta (Vektor®)+TX, Epicoccum nigrum+TX, Epicoccum purpurascens+TX, Epicoccum spp.+TX, Filobasidium floriforme+TX, Fusarium acuminatum+TX, Fusarium chlamydosporum+TX, Fusarium oxysporum (Fusaclean®/Biofox C®)+TX, Fusarium proliferatum+TX, Fusarium spp.+TX, Galactomyces geotrichum+TX, Gliocladium catenulatum (Primastop®+TX, Prestop®)+TX, Gliocladium roseum+TX, Gliocladium spp. (SoilGard®)+TX, Gliocladium virens (Soilgard®)+TX, Granulovirus (Granupom®)+TX, Halobacillus halophilus+TX, Halobacillus litoralis+TX, Halobacillus trueperi+TX, Halomonas spp.+TX, Halomonas subglaciescola+TX, Halo vibrio variabilis+TX, Hanseniaspora uvarum+TX, Helicoverpa armigera nucleopolyhedrovirus (Helicovex®)+TX, Helicoverpa zea nuclear polyhedrosis virus (Gemstar®)+TX, Isoflavone—formononetin (Myconate®)+TX, Kloeckera apiculata+TX, Kloeckera spp.+TX, Lagenidium giganteum (Laginex®)+TX, Lecanicillium longisporum (Vertiblast®)+TX, Lecanicillium muscarium (Vertikil®)+TX, Lymantria Dispar nucleopolyhedrosis virus (Disparvirus®)+TX, Marinococcus halophilus+TX, Meira geulakonigii+TX, Metarhizium anisopliae (Met52®)+TX, Metarhizium anisopliae (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibacillus marismortui*+TX, *Xanthomonas campestris* pv. *Poae* (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of Labiatae (Botania®)+TX, extracts of clove rosemary peppermint and thyme oil (Garden Insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove peppermint garlic oil and mint (Soil Shot®)+TX, kaolin (Screen®)+TX, storage glucam of brown algae (Laminarin®)+TX; and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M Oriental Fruit Moth Sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, Tetradecatrienyl acetate+TX, 13-Hexadecatrienal+TX, (E+TX,Z)-7+TX, 9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (*Aphelinus*-System®)+TX, *Acerophagus papaya*+TX, *Adalia bipunctata* (*Adalia*-System®)+TX, *Adalia bipunctata* (Adaline®)+TX, *Adalia bipunctata* (Aphidalia®)+TX, *Ageniaspis citricol*+TX, *Ageniaspis fuscicollis*+TX, *Amblyseius andersoni* (Anderline®+TX, Andersoni-System®)+TX, *Amblyseius califomicus* (Amblyline®+TX, Spical®)+TX, *Amblyseius cucumeris* (Thripex®+TX, Bugline *cucumeris*®)+TX, *Amblyseius fallacis* (Fallacis®)+TX, *Amblyseius swirskii* (Bugline *swirskii*®+TX, Swirskii-Mite®)+TX, *Amblyseius womersleyi* (WomerMite®)+TX,

*Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (*Anthocoris*-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chlysoperla camea* (Chrysoline®)+TX, *Chrysoperla camea* (Chrysopa®)+TX, *Chlysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (*Delphastus*®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (Encarsia Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®))+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, *Formononetin* (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®))+TX, *Heterorhabditis megidis* (Nemasys H®+TX, BioNem H®+TX, Exhibitline hm®+TX, Larvanem-M®))+TX, *Hippodamia convergens*+TX, *Hypoaspis aculeifer* (Aculeifer-System®+TX, Entomite-A®))+TX, *Hypoaspis miles* (Hypoline m®+TX, Entomite-M®))+TX, *Lbalia leucospoides*+TX, *Lecanoideus flocissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus califomicus*+TX, *Neoseiulus cucumeris* (THRYPEX®))+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline i®)+TX, *Orius laevigatus* (Thripor-L®+TX, Oriline I®)+TX, *Orius majusculus* (Oriline m®))+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffee*+TX, *Phytoseiulus macropilus*+TX, *Phytoseiulus persimilis* (Spidex®+TX, Phytoline p®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+*TX*, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, *Steinernema*-System®+TX, NemAttack®+TX, Nemaplus®+TX, Exhibitline sf®+TX, Scia-rid®+TX, Entonem®)+TX, *Steinernema kraussei* (Nemasys L®+TX, BioNem L®+TX, Exhibitline srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Harpin) (ProAct®+TX, Ni-HIB IT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zeno+TX, Pheromone trap (Thripline ams®)+TX, potassium bicarbonate (MilStop®)+TX, potassium salts of fatty acids (Sanova®)+TX, potassium silicate solution (Sil-Matrix®)+TX, potassium iodide+potassiumthiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright@ 1995-2013]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used.

The active ingredient mixture of the compounds of formula I selected from Tables 1 to 23 and P with active ingredients described above comprises a compound selected from Tables 1 to 23 and P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are ratios by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1 to 23 and P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 23 and P and the active ingredients as described above is not essential for working the present invention.

BIOLOGICAL EXAMPLES

Example B1: *Bemisia tabaci* (Cotton White Fly): Feeding/Contact Activity

Cotton leaf discs were placed on agar in 24-well microtiter plates and sprayed with aqueous test solutions prepared from 10'000 ppm DMSO stock solutions. After drying the leaf discs were infested with adult white flies. The samples were checked for mortality 6 days after incubation.

The following compounds resulted in at least 80% mortality at an application rate of 200 ppm:
P5, P6, P8, P9, P10, P12, P13, P15 and P16.

Example B2: *Diabrotica Balteata* (Corn Root Worm)

Maize sprouts placed onto an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm:
P1, P3, P5, P6, P7, P8, P9, P10, P11, P12, P13, P15, P16 and P17.

Example B3: *Euschistus heros* (Neotropical Brown Stink Bug)

Soybean leaves on agar in 24-well microtiter plates were sprayed with aqueous test solutions prepared from 10'000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm:
P1, P3, P5, P7, P8, P9, P10, P11, P12, P13, P14, P15 and P16.

Example B4: *Frankliniella occidentalis* (Western Flower *Thrips*): Feeding/Contact Activity Sunflower leaf discs were placed on agar in 24-well microtiter plates and sprayed with aqueous test solutions prepared from 10'000 DMSO stock solutions. After drying the leaf discs were infested with a *Frankliniella* population of mixed ages. The samples were assessed for mortality 7 days after infestation. The following compounds resulted in at least 80% mortality at an application rate of 200 ppm: P8, P9 and P10.

Example B5: *Myzus persicae* (Green Peach Aphid): Feeding/Contact Activity

Sunflower leaf discs were placed onto agar in a 24-well microtiter plate and sprayed with aqueous test solutions prepared from 10'000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm:
P3, P5, P6, P8, P9, P10, P11, P12, P13, P14, P15, P16 and P17.

Example B6: *Myzus persicae* (Green Peach Aphid). Systemic Activity

Roots of pea seedlings infested with an aphid population of mixed ages were placed directly into aqueous test solutions prepared from 10'000 DMSO stock solutions. The samples were assessed for mortality 6 days after placing seedlings into test solutions.

The following compounds resulted in at least 80% mortality at a test rate of 24 ppm:
P2, P8, P9, P10, P12, P14 and P15.

Example B7: *Plutella xylostella* (Diamond Back Moth)

24-well microtiter plates with artificial diet were treated with aqueous test solutions prepared from 10'000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:
P1, P3, P6, P7, P8, P9, P10, P11, P12, P13, P15 and P16.

Example B8: *Spodoptera littoralis* (Egyptian Cotton Leaf Worm)

Cotton leaf discs were placed onto agar in 24-well microtiter plates and sprayed with aqueous test solutions prepared from 10'000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm:
P3, P5, P6, P7, P8, P9, P10, P11, P13, P15 and P16.

Example B9: *Spodoptera littoralis* (Egyptian Cotton Leaf Worm)

Test compounds were applied by pipette from 10'000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compounds gave an effect of at least 80% in at least one of the three categories (mortality, anti-feeding, or growth inhibition) at a test rate of 12.5 ppm:
P3, P5, P8, P9, P10, P15 and P16.

Example B10: *Tetranychus urticae* (Two-Spotted Spider Mite): Feeding/Contact Activity Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm:
P8

Example B11: *Thrips tabaci* (Onion *Thrips*) Feeding/Contact Activity

Sunflower leaf discs were placed on agar in 24-well microtiter plates and sprayed with aqueous test solutions prepared from 10'000 ppm DMSO stock solutions. After drying the leaf discs were infested with a *thrips* population of mixed ages. The samples were assessed for mortality 6 days after infestation.

The following compounds resulted in at least 80% mortality at an application rate of 200 ppm:
P5, P6, P8, P9, P10, P15 and P16.

Example B12: *Aedes aegypti* (Yellow Fever Mosquito)

Test solutions, at an application rate of 200 ppm in ethanol, were applied to 12 well tissue culture plates. Once the deposits were dry, five, two to five day old adult female *Aedes aegypti* were added to each well, and sustained with a 10% sucrose solution in a cotton wool plug. Assessment of knockdown was made one hour after introduction, and mortality was assessed at 24 and 48 hours after introduction.

The following compounds gave at least 80% control of *Aedes aegypti* after 48 h and/or 24 h:
P5, P8, P9, P10, P11, P13, P15 and P16.

Example B13: *Anopheles stephensi* (Indian Malaria Mosquito)

Test solutions, at an application rate of 200 ppm in ethanol, were applied to 12 well tissue culture plates. Once the deposits were dry, five, two to five day old adult female *Anopheles stephensi* were added to each well, and sustained with a 10% sucrose solution in a cotton wool plug. Assessment of knockdown was made one hour after introduction, and mortality was assessed at 24 and 48 hours after introduction.

The following compounds gave at least 80% control of *Anopheles stephensi* after 48 h and/or 24 h:
P5, P8, P9, P10, P11, P13, P15 and P16.

The invention claimed is:
1. A compound of formula I,

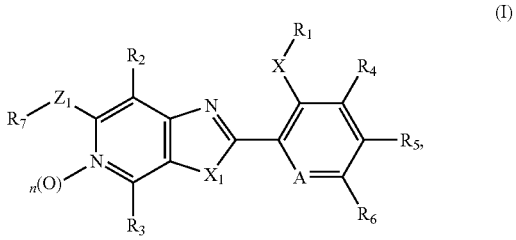

wherein
A is CH, N, or NO;
X is S, SO or $SO_2$;
$X_1$ is O, S, or $N(C_1$-$C_3$alkyl);
$R_1$ is $C_1$-$C_6$alkyl, $C_1$-$C_6$haloalkyl, $C_3$-$C_6$cycloalkyl, $C_3$-$C_6$cycloalkyl-$C_1$-$C_6$alkyl; or
$R_1$ is $C_3$-$C_6$cycloalkyl-$C_1$-$C_6$alkyl mono- or polysubstituted by substituents selected from the group consisting of halogen, cyano and $C_1$-$C_4$alkyl; or
$R_1$ is $C_2$-$C_6$alkenyl, $C_2$-$C_6$haloalkenyl or $C_2$-$C_6$alkynyl;
$R_2$ is hydrogen, or $C_1$-$C_3$alkyl;
$R_3$ is hydrogen, or $C_1$-$C_3$alkyl;
$R_4$ and $R_6$ is hydrogen or $C_1$-$C_3$alkyl;
$R_5$ is hydrogen, halogen, $C_1$-$C_6$alkyl, $C_1$-$C_6$haloalkyl, $C_1$-$C_6$haloalkoxy, $C_1$-$C_6$alkylsulfanyl, $C_1$-$C_6$alkylsulfinyl, $C_1$-$C_6$alkylsulfonyl, $C_1$-$C_6$haloalkylsulfanyl, $C_1$-$C_6$haloalkylsulfinyl, $C_1$-$C_6$haloalkylsulfonyl, or $C_3$-$C_6$cycloalkyl-$C_1$-$C_4$alkyl;

$Z_1$ is oxygen, S, SO or $SO_2$, with the proviso that when $R_7$ is hydrogen, $Z_1$ is different from SO and $SO_2$;

$R_7$ is $C_1$-$C_6$haloalkyl, $C_2$-$C_6$alkenyl, $C_2$-$C_6$haloalkenyl or $C_2$-$C_6$alkynyl, $C_2$-$C_6$haloalkynyl, $C_1$-$C_6$alkylcyano, $C_3$-$C_6$cycloalkyl, $C_3$-$C_6$halocycloalkyl, $C_3$-$C_6$cycloalkyl-$C_1$-$C_4$alkyl, or $C_3$-$C_6$cycloalkyl-$C_1$-$C_4$alkyl mono- or polysubstituted by substituents selected from the group consisting of halogen, cyano and $C_1$-$C_4$alkyl;

n is 0 or 1; or an agrochemically acceptable salt, a stereoisomer, an enantiomer, a tautomer or an N-oxide of those compounds.

2. The compound of claim 1, represented by the compounds of formula I-1

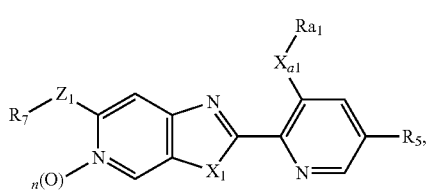

(I-1)

wherein $X_{a1}$ is S, SO or $SO_2$;

$R_{a1}$ is methyl, ethyl, n-propyl, i-propyl or cyclopropylmethyl; or an agrochemically acceptable salt, a stereoisomer, an enantiomer, or a tautomer of those compounds.

3. The compound of claim 1, represented by the compounds of formula I-2,

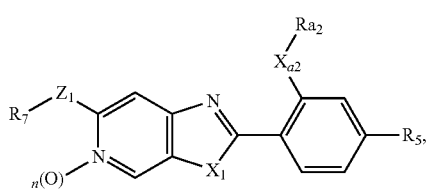

(I-2)

wherein $X_{a2}$ is S, SO or $SO_2$;

$R_{a2}$ is methyl, ethyl, n-propyl, i-propyl or cyclopropylmethyl; or an agrochemically acceptable salt, a stereoisomer, an enantiomer, or a tautomer of those compounds.

4. The compound of claim 1, wherein

A is N;

X is S or $SO_2$;

$X_1$ is N($C_1$-$C_3$alkyl);

$R_1$ is $C_1$-$C_6$alkyl;

$R_2$, $R_3$, $R_4$ and $R_6$ are hydrogen;

$Z_1$ is oxygen, S, SO or $SO_2$;

$R_5$ is $C_1$-$C_4$haloalkyl or halogen; and $R_7$ is $C_1$-$C_4$alkylcyano, or $R_7$ is $C_1$-$C_4$haloalkyl.

5. The compound of claim 1, wherein $Z_1$ is S, SO or $SO_2$.

6. The compound of claim 1, wherein $R_5$ is halogen or $C_1$-$C_6$haloalkyl.

7. An insecticidal, acaricidal, nematicidal or molluscicidal composition, comprising an insecticidally, acaricidally, nematicidally or molluscicidally effective amount of a compound of formula I according to claim 1 and a suitable carrier or diluent therefor.

8. A method of combating and controlling pests which comprises applying a pesticidally effective amount of a compound of formula I

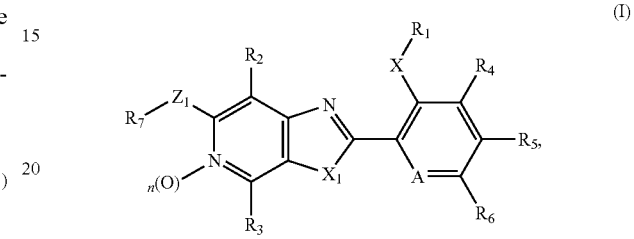

(I)

wherein

A is CH, N, or NO;

X is S, SO or $SO_2$;

$X_1$ is O, S, or N($C_1$-$C_3$alkyl); $R_1$ is $C_1$-$C_6$alkyl, $C_1$-$C_6$haloalkyl, $C_3$-$C_6$cycloalkyl, $C_3$-$C_6$cycloalkyl-$C_1$-$C_6$alkyl; or $R_1$ is $C_3$-$C_6$cycloalkyl-$C_1$-$C_6$alkyl mono- or polysubstituted by substituents selected from the group consisting of halogen, cyano and $C_1$-$C_4$alkyl; or $R_1$ is $C_2$-$C_6$alkenyl, $C_2$-$C_6$haloalkenyl or $C_2$-$C_6$alkynyl;

$R_2$ is hydrogen, or $C_1$-$C_3$alkyl;

$R_3$ is hydrogen, or $C_1$-$C_3$alkyl;

$R_4$ and $R_6$ is hydrogen or $C_1$-$C_3$alkyl;

$R_5$ is hydrogen, halogen, $C_1$-$C_6$alkyl, $C_1$-$C_6$haloalkyl, $C_1$-$C_6$haloalkoxy, $C_1$-$C_6$alkylsulfanyl, $C_1$-$C_6$alkylsulfinyl, $C_1$-$C_6$alkylsulfonyl, $C_1$-$C_6$haloalkylsulfanyl, $C_1$-$C_6$haloalkylsulfinyl, $C_1$-$C_6$haloalkylsulfonyl, or $C_3$-$C_6$cycloalkyl-$C_1$-$C_4$alkyl;

$Z_1$ is oxygen, S, SO or $SO_2$, with the proviso that when $R_7$ is hydrogen, $Z_1$ is different from SO and $SO_2$;

$R_7$ is hydrogen, $C_1$-$C_6$alkyl, —$C_1$-$C_6$haloalkyl, $C_2$-$C_6$alkenyl, $C_2$-$C_6$haloalkenyl or $C_2$-$C_6$alkynyl, $C_2$-$C_6$haloalkynyl, $C_1$-$C_6$alkylcyano, $C_3$-$C_6$cycloalkyl, $C_3$-$C_6$halocycloalkyl, $C_3$-$C_6$cycloalkyl-$C_1$-$C_4$alkyl, or $C_3$-$C_6$cycloalkyl-$C_1$-$C_4$alkyl mono- or polysubstituted by substituents selected from the group consisting of halogen, cyano and $C_1$-$C_4$alkyl;

n is 0 or 1; or an agrochemically acceptable salt, a stereoisomer, an enantiomer, a tautomer or an N-oxide of those compounds, or of a composition comprising such a compound, to a pest, to a locus of a pest, or to a plant susceptible to attack by a pest.

9. The method of claim 8, which comprises applying the pesticidal composition to a pest, to a locus of a pest, or to a plant susceptible to attack by a pest.

10. A compound of formula I,

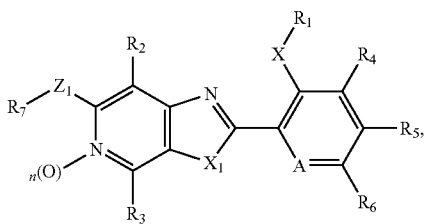

wherein
A is N or NO;
X is S, SO or $SO_2$;
$X_1$ is O, S, or $N(C_1\text{-}C_3\text{alkyl})$;
$R_1$ is $C_1\text{-}C_6\text{alkyl}$, $C_1\text{-}C_6\text{haloalkyl}$, $C_3\text{-}C_6\text{cycloalkyl}$, $C_3\text{-}C_6\text{cycloalkyl-}C_1\text{-}C_6\text{alkyl}$; or
$R_1$ is $C_3\text{-}C_6\text{cycloalkyl-}C_1\text{-}C_6\text{alkyl}$ mono- or polysubstituted by substituents selected from the group consisting of halogen, cyano and $C_1\text{-}C_4\text{alkyl}$; or
$R_1$ is $C_2\text{-}C_6\text{alkenyl}$, $C_2\text{-}C_6\text{haloalkenyl}$ or $C_2\text{-}C_6\text{alkynyl}$;
$R_2$ is hydrogen, or $C_1\text{-}C_3\text{alkyl}$;
$R_3$ is hydrogen, or $C_1\text{-}C_3\text{alkyl}$;
$R_4$ and $R_6$ is hydrogen or $C_1\text{-}C_3\text{alkyl}$;
$R_5$ is hydrogen, halogen, $C_1\text{-}C_6\text{alkyl}$, $C_1\text{-}C_6\text{haloalkyl}$, $C_1\text{-}C_6\text{haloalkoxy}$, $C_1\text{-}C_6\text{alkylsulfanyl}$, $C_1\text{-}C_6\text{alkylsulfinyl}$, $C_1\text{-}C_6\text{alkylsulfonyl}$, $C_1\text{-}C_6\text{haloalkylsulfanyl}$, $C_1\text{-}C_6\text{haloalkylsulfinyl}$, $C_1\text{-}C_6\text{haloalkylsulfonyl}$, or $C_3\text{-}C_6\text{cycloalkyl-}C_1\text{-}C_4\text{alkyl}$;
$Z_1$ is oxygen, S, SO or $SO_2$, with the proviso that when $R_7$ is hydrogen, $Z_1$ is different from SO and $SO_2$;
$R_7$ is hydrogen, $C_1\text{-}C_6\text{alkyl}$, $C_1\text{-}C_6\text{haloalkyl}$, $C_2\text{-}C_6\text{alkenyl}$, $C_2\text{-}C_6\text{haloalkenyl}$ or $C_2\text{-}C_6\text{alkynyl}$, $C_2\text{-}C_6\text{haloalkynyl}$, $C_1\text{-}C_6\text{alkylcyano}$, $C_3\text{-}C_6\text{cycloalkyl}$, $C_3\text{-}C_6\text{halocycloalkyl}$, $C_3\text{-}C_6\text{cycloalkyl-}C_1\text{-}C_4\text{alkyl}$, or $C_3\text{-}C_6\text{cycloalkyl-}C_1\text{-}C_4\text{alkyl}$ mono- or polysubstituted by substituents selected from the group consisting of halogen, cyano and $C_1\text{-}C_4\text{alkyl}$;
n is 0 or 1; or an agrochemically acceptable salt, a stereoisomer, an enantiomer, a tautomer or an N-oxide of those compounds.

* * * * *